US010596195B2

(12) United States Patent
Cantor et al.

(10) Patent No.: US 10,596,195 B2
(45) Date of Patent: Mar. 24, 2020

(54) DISCOVERY OF REGULATORY T CELLS PROGRAMMED TO SUPPRESS AN IMMUNE RESPONSE

(71) Applicant: Dana-Farber Cancer Institute, Inc., Boston, MA (US)

(72) Inventors: Harvey Cantor, Boston, MA (US); Hye-Jung Kim, Brookline, MA (US); Linrong Lu, Hangzhou (CN)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 15/405,434

(22) Filed: Jan. 13, 2017

(65) Prior Publication Data

US 2017/0224732 A1    Aug. 10, 2017

Related U.S. Application Data

(62) Division of application No. 13/878,894, filed as application No. PCT/US2011/056746 on Oct. 18, 2011, now abandoned.

(60) Provisional application No. 61/405,696, filed on Oct. 22, 2010.

(51) Int. Cl.
| | | |
|---|---|---|
| *A61K 35/26* | (2015.01) | |
| *A61K 35/17* | (2015.01) | |
| *A61K 39/00* | (2006.01) | |
| *C12N 5/0783* | (2010.01) | |
| *A61K 9/00* | (2006.01) | |
| *A61K 38/20* | (2006.01) | |
| *C07K 16/24* | (2006.01) | |
| *C07K 16/28* | (2006.01) | |
| *A61K 35/12* | (2015.01) | |

(52) U.S. Cl.
CPC .......... *A61K 35/17* (2013.01); *A61K 9/0019* (2013.01); *A61K 38/2086* (2013.01); *A61K 39/0008* (2013.01); *A61K 39/0011* (2013.01); *C07K 16/244* (2013.01); *C07K 16/2803* (2013.01); *C12N 5/0637* (2013.01); *A61K 2035/122* (2013.01); *A61K 2035/124* (2013.01); *A61K 2039/5152* (2013.01); *A61K 2039/5158* (2013.01); *A61K 2039/55522* (2013.01); *C07K 2317/31* (2013.01); *C07K 2317/75* (2013.01); *C12N 2501/2315* (2013.01); *C12N 2501/2321* (2013.01); *C12N 2502/1114* (2013.01)

(58) Field of Classification Search
None
See application file for complete search history.

(56) References Cited

U.S. PATENT DOCUMENTS

| | | | |
|---|---|---|---|
| 5,552,303 A | 9/1996 | Grabstein et al. | |
| 6,780,843 B2 | 8/2004 | Lin et al. | |
| 9,783,846 B2 * | 10/2017 | Olek ..................... | C12Q 1/686 |
| 2002/0022030 A1 | 2/2002 | Marrack et al. | |
| 2007/0081991 A1 | 4/2007 | Soderstrom | |
| 2007/0160578 A1 | 7/2007 | Waldmann et al. | |
| 2008/0152642 A1 | 6/2008 | Georgopoulos et al. | |
| 2009/0155292 A1 | 6/2009 | Santamaria et al. | |
| 2009/0238791 A1 | 9/2009 | Jacques et al. | |
| 2009/0324538 A1 | 12/2009 | Wong et al. | |
| 2010/0260781 A1 | 10/2010 | Murray | |
| 2013/0157363 A1 | 6/2013 | Kim et al. | |
| 2013/0302276 A1 | 11/2013 | Cantor et al. | |
| 2013/0317113 A1 | 11/2013 | Hadlock et al. | |
| 2014/0220012 A1 | 8/2014 | Noelle et al. | |
| 2014/0335530 A1 | 11/2014 | Drake et al. | |
| 2015/0250862 A1 | 9/2015 | Cantor et al. | |
| 2017/0269076 A1 | 9/2017 | Cantor et al. | |

FOREIGN PATENT DOCUMENTS

| | | |
|---|---|---|
| WO | WO 2006/063974 A2 | 6/2006 |
| WO | WO 2007/110230 A2 | 10/2007 |
| WO | WO 2007/110230 A3 | 10/2007 |
| WO | WO 2007/136518 A2 | 11/2007 |
| WO | WO2007136518     * | 11/2007 |
| WO | WO 2008/101272 A1 | 8/2008 |
| WO | WO 2008/109852 A2 | 9/2008 |
| WO | WO 2009/002562 A2 | 12/2008 |
| WO | WO 2009/027284 A1 | 3/2009 |
| WO | WO 2010/071836 A1 | 6/2010 |
| WO | WO 2012/054509 A2 | 4/2012 |
| WO | WO 2012/079000 A1 | 6/2012 |
| WO | WO 2014/039513 A2 | 3/2014 |

(Continued)

OTHER PUBLICATIONS

Partial Supplementary European Search Report for EP11835009.9 dated Jan. 12, 2015.
Extended European Search Report for EP11835009.9 dated May 13, 2015.
Corrected European Search Opinion for EP11835009.9 dated Jun. 19, 2015.

(Continued)

*Primary Examiner* — Michail A Belyavskyi
(74) *Attorney, Agent, or Firm* — Wolf, Greenfield & Sacks, P.C.

(57) ABSTRACT

A method to treat an autoimmune disease is provided. The method involves administration of interleukin-15 receptor (IL-15R) agonists in an amount effective to ameliorate a symptom of the autoimmune disease. The invention also involves a method to treat an autoimmune disease by ex-vivo expansion of CD44+CD122+Kir+ CD8+ Treg cells and administration of the CD44+CD122+Kir+ CD8+ Treg cells. Compositions comprising CD44+CD122+Kir+ CD8+ Treg cells are also provided. Methods for stimulating an immune response to an antigen are also provided.

8 Claims, 15 Drawing Sheets

Specification includes a Sequence Listing.

(56) References Cited

FOREIGN PATENT DOCUMENTS

| WO | WO 2014/039513 A3 | 3/2014 |
|----|-------------------|--------|
| WO | WO 2014/052454 A2 | 4/2014 |
| WO | WO 2014/183056 A1 | 11/2014 |
| WO | WO 2014/058915 A1 | 4/2017 |

OTHER PUBLICATIONS

Invitation to Pay Additional Fees for PCT/US2011/056746 dated Feb. 21, 2012.
International Search Report and Written Opinion for PCT/US2011/056746 dated May 1, 2012.
International Preliminary Report on Patentability for PCT/US2011/056746 dated May 2, 2013.
Invitation to Pay Additional Fees for PCT/US2013/61851 dated Jan. 31, 2014.
International Search Report and Written Opinion for PCT/US2013/61851 dated Apr. 10, 2014.
International Preliminary Report on Patentability for PCT/US2013/061851 dated Jun. 25, 2015.
International Search Report and Written Opinion for PCT/US2016/035692 dated Sep. 13, 2016.
Almeida et al., Competition controls the rate of transition between the peripheral pools of CD4+CD25− and CD4+CD25+ T cells. Int Immunol. Nov. 2006;18(11):1607-13. Epub Sep. 20, 2006.
Anderton et al., Negative selection during the peripheral immune response to antigen. J Exp Med. Jan. 1, 2001;193(1):1-11.
Anfossi et al., Biology of T memory type 1 cells. Immunol Rev. Jun. 2001;181:269-78.
Anfossi et al., Expansion and function of CD8+ T cells expressing Ly49 inhibitory receptors specific for MHC class I molecules. J Immunol. Sep. 15, 2004;173(6):3773-82.
Arvey et al., Inflammation-induced repression of chromatin bound by the transcription factor Foxp3 in regulatory T cells. Nat Immunol. Jun. 2014;15(6):580-7. doi: 10.1038/ni.2868. Epub Apr. 13, 2014.
Bernard et al., Identification of an interleukin-15alpha receptor-binding site on human interleukin-15. J Biol Chem. Jun. 4, 2004;279(23):24313-22. Epub Mar. 23, 2004.
Beyer et al., Regulatory T cells in cancer. Blood. Aug. 1, 2006;108(3):804-11.
Blackburn et al., Selective expansion of a subset of exhausted CD8 T cells by alphaPD-L1 blockade. Proc Natl Acad Sci U S A. Sep. 30, 2008;105(39):15016-21. doi: 10.1073/pnas.0801497105. Epub Sep. 22, 2008.
Bouneaud et al., Impact of negative selection on the T cell repertoire reactive to a self-peptide: a large fraction of T cell clones escapes clonal deletion. Immunity. Dec. 2000;13(6):829-40.
Bubier et al., Treatment of BXSB-Yaa mice with IL-21R-Fc fusion protein minimally attenuates systemic lupus erythematosus. Ann N Y Acad Sci. Sep. 2007;1110:590-601.
Burchill et al., Distinct effects of STAT5 activation on CD4+ and CD8+ T cell homeostasis: development of CD4+CD25+ regulatory T cells versus CD8+ memory T cells. J Immunol. Dec. 1, 2003;171(11):5853-64.
Burchill et al., IL-2 receptor beta-dependent STAT5 activation is required for the development of Foxp3+ regulatory T cells. J Immunol. Jan. 1, 2007;178(1):280-90.
Burchill et al., Linked T cell receptor and cytokine signaling govern the development of the regulatory T cell repertoire. Immunity. Jan. 2008;28(1):112-21. doi: 10.1016/j.immuni.2007.11.022.
Cai et al., Helios deficiency has minimal impact on T cell development and function. J Immunol. Aug. 15, 2009;183(4):2303-11. doi: 10.4049/jimmunol.0901407. Epub Jul. 20, 2009.
Cantor, Definition of a Sublineage of CD8 Cells Programmed to Exert Regulatory Activity: CD8+ Treg. Presentation given on Jun. 14, 2009. FOCIS Meeting, San Francisco CA. 5 Pages.
Cantor, Definition of a Sublineage of CD8 Cells Programmed to Exert Regulatory Activity: CD8+ Treg. Presentation given on Sep. 4, 2009. Pasteur Institute, Paris, FR. 7 Pages.
Cantor, Definition of a Sublineage of CD8 Cells Programmed to Maintain Self Tolerance: CD8+ Treg. Presentation given on Nov. 2, 2009. Northwestern, Chicago IL. 7 Pages.
Cantor, Development of T cell subsets and self-tolerance. Presentation given on Dec. 2, 2008. PARC/ Ragon Institute, Cambridge, MA. 12 Pages.
Cantor, Regulation of follicular helper cells by Opn+ dendritic cells and CD8+ regulatory cells. Presentation given on Aug. 2, 2010. FASEB Summer Conference, Steamboat Springs, CO. 49 Pages.
Cantor, Suppressor cells revisited: CD8+ Treg. Presentation given on Aug. 30, 2009. ESOT, Paris, FR. 7 Pages.
Cantor, Therapeutic use of anti-NKG2A F(ab)2 in the context of EAE/MS and RA. Therapeutic manipulation of CD8+ Treg in the context of SLE. Presentation given on Nov. 12, 2009. Copenhagen, DK. 91 Pages.
Chen et al., Preferential development of CD4 and CD8 T regulatory cells in RasGRP1-deficient mice. J Immunol. May 1, 2008;180(9):5973-82.
Chen et al., Regulatory T cell clones induced by oral tolerance: suppression of autoimmune encephalomyelitis. Science. Aug. 26, 1994;265(5176):1237-40.
Chwae et al., Molecular mechanism of the activation-induced cell death inhibition mediated by a p70 inhibitory killer cell Ig-like receptor in Jurkat T cells. J Immunol. Oct. 1, 2002;169(7):3726-35.
Coles et al., Memory CD8 T lymphocytes express inhibitory MHC-specific Ly49 receptors. Eur J Immunol. Jan. 2000;30(1):236-44.
Crew et al., An HLA-E single chain trimer inhibits human NK cell reactivity towards porcine cells. Mol Immunol. Jun. 2005;42(10):1205-14. Epub Jan. 8, 2005.
Curiel et al., Specific recruitment of regulatory T cells in ovarian carcinoma fosters immune privilege and predicts reduced survival. Nat Med. Sep. 2004;10(9):942-9. Epub Aug. 22, 2004.
D'Andrea et al., Regulation of T cell lymphokine production by killer cell inhibitory receptor recognition of self HLA class I alleles. J Exp Med. Aug. 1, 1996;184(2):789-94.
Davies et al., A peptide from heat shock protein 60 is the dominant peptide bound to Qa-1 in the absence of the MHC class Ia leader sequence peptide Qdm. J Immunol. May 15, 2003;170(10):5027-33.
Feng et al., Control of the inheritance of regulatory T cell identity by a cis element in the Foxp3 locus. Cell. Aug. 14, 2014;158(4):749-63. doi: 10.1016/j.cell.2014.07.031.
Fontenot et al., A function for interleukin 2 in Foxp3-expressing regulatory T cells. Nat Immunol. Nov. 2005;6(11):1142-51. Epub Oct. 16, 2005. Erratum in: Nat Immunol. Apr. 2006;7(4):427.
Fu et al., A multiply redundant genetic switch 'locks in' the transcriptional signature of regulatory T cells. Nat Immunol. Oct. 2012;13(10):972-80. doi: 10.1038/ni.2420. Epub Sep. 9, 2012.
Gati et al., CD158 receptor controls cytotoxic T-lymphocyte susceptibility to tumor-mediated activation-induced cell death by interfering with Fas signaling. Cancer Res. Nov. 2003;63(21):7475-82.
Goldrath et al., Selecting and maintaining a diverse T-cell repertoire. Nature. Nov. 18, 1999;402(6759):255-62.
Gray et al., The BH3-only proteins Bim and Puma cooperate to impose deletional tolerance of organ-specific antigens. Immunity. Sep. 21, 2012;37(3):451-62. doi: 10.1016/j.immuni.2012.05.030. Epub Sep. 6, 2012.
Groux et al., A CD4+ T-cell subset inhibits antigen-specific T-cell responses and prevents colitis. Nature. Oct. 16, 1997;389(6652):737-42.
Groux et al., Interleukin-10 induces a long-term antigen-specific anergic state in human CD4+ T cells. J Exp Med. Jul. 1, 1996;184(1):19-29.
Hayashi et al., Germ cell specification in mice. Science. Apr. 20, 2007;316(5823):394-6.
Hill et al., Foxp3 transcription-factor-dependent and -independent regulation of the regulatory T cell transcriptional signature. Immunity. Nov. 2007;27(5):786-800.
Hoffmann et al., Isolation of CD4+CD25+ regulatory T cells for clinical trials. Biol Blood Marrow Transplant. Mar. 2006;12(3):267-74.
Hong et al., High-dose cyclophosphamide-mediated anti-tumor effects by the superior expansion of CD44(high) cells after their

(56) References Cited

OTHER PUBLICATIONS selective depletion. Immunobiology. Mar. 2010;215(3):182-93. doi: 10.1016/j.imbio.2009.01.010. Epub May 22, 2009.
Horsley et al., Blimp1 defines a progenitor population that governs cellular input to the sebaceous gland. Cell. Aug. 11, 2006;126(3):597-609.
Inobe et al., IL-4 is a differentiation factor for transforming growth factor-beta secreting Th3 cells and oral administration of IL-4 enhances oral tolerance in experimental allergic encephalomyelitis. Eur J Immunol. Sep. 1998;28(9):2780-90.
Izui et al., The Y chromosome from autoimmune BXSB/MpJ mice induces a lupus-like syndrome in (NZW × C57BL/6)F1 male mice, but not in C57BL/6 male mice. Eur J Immunol. Jun. 1988;18(6):911-5.
Jiang et al., Regulatory CD8+ T cells fine-tune the myelin basic protein-reactive T cell receptor V beta repertoire during experimental autoimmune encephalomyelitis. Proc Natl Acad Sci USA. Jul. 8, 2003;100(14):8378-83. Epub Jun. 24, 2003.
Jin et al., Role of PD-1 in regulating T-cell immunity. Curr Top Microbiol Immunol. 2011;350:17-37. doi: 10.1007/82_2010_116.
Judge et al., Interleukin 15 controls both proliferation and survival of a subset of memory-phenotype CD8(+) T cells. J Exp Med. Oct. 7, 2002;196(7):935-46.
Kearney et al., Visualization of peptide-specific T cell immunity and peripheral tolerance induction in vivo. Immunity. Jul. 1994;1(4):327-39.
Kikuchi et al., Differential role of three major New Zealand Black-derived loci linked with Yaa-induced murine lupus nephritis. J Immunol. Jan. 15, 2005;174(2):1111-7.
Kim et al., CD8+ T regulatory cells express the Ly49 Class I MHC receptor and are defective in autoimmune prone B6-Yaa mice. Proc Natl Acad Sci U S A. Feb. 1, 2011;108(5):2010-5. doi: 10.1073/pnas.1018974108. Epub Jan. 13, 2011.
Kim et al., Inhibition of follicular T-helper cells by CD8(+) regulatory T cells is essential for self tolerance. Nature. Sep. 16, 2010;467(7313):328-32.
Kim et al., Regulatory T cells prevent catastrophic autoimmunity throughout the lifespan of mice. Nat Immunol. Feb. 2007;8(2):191-7. Epub Nov. 30, 2006.
Kim et al., Stable inhibitory activity of regulatory T cells requires the transcription factor Helios. Science. Oct. 16, 2015;350(6258):334-9. doi: 10.1126/science.aad0616.
Kim, CD8+ Treg and Autoimmunity. The 4th Symposium of Immunological Self. Division of Immunology Seminar, HMS. Presentation given on Jan. 27, 2012. Kyoto, Japan. 8 Pages.
Kim, Qa-1 restricted CD8+ Treg and Autoimmunity. The 4th Symposium of Immunological Self Division of Immunology Seminar, HMS. Presentation given on Apr. 27, 2012. Division of Immunology Seminar Series, Harvard Medical School, Boston MA. 9 Pages.
Kim, Shaping of antibody responses by CD8+ Regulatory T Cells. The 4th Symposium of Immunological Self. Division of Immunology Seminar, HMS. Presentation given on Nov. 29, 2011. German Rheumatology Research Institute, Berlin, Germany. 9 Pages.
Kitagawa et al., Molecular determinants of regulatory T cell development: the essential roles of epigenetic changes. Front Immunol. May 10, 2013;4:106. doi: 10.3389/fimmu.2013.00106. eCollection 2013.
Kurachi et al., The transcription factor BATF operates as an essential differentiation checkpoint in early effector CD8+ T cells. Nat Immunol. Apr. 2014;15(4):373-83. doi: 10.1038/ni.2834. Epub Mar. 2, 2014.
Laurence et al., Interleukin-2 signaling via STAT5 constrains T helper 17 cell generation. Immunity. Mar. 2007;26(3):371-81.
Leavenworth et al., Amelioration of arthritis through mobilization of peptide-specific CD8+ regulatory T cells. J Clin Invest. Mar. 1, 2013;123(3):1382-9. doi: 10.1172/JCI66938. Epub Feb. 8, 2013.
Leavenworth et al., Analysis of the cellular mechanism underlying inhibition of EAE after treatment with anti-NKG2A F(ab')2. Proc Natl Acad Sci U S A. Feb. 9, 2010;107(6):2562-7. doi: 10.1073/pnas.0914732107. Epub Jan. 21, 2010.
Leavenworth et al., Mobilization of natural killer cells inhibits development of collagen-induced arthritis. Proc Natl Acad Sci U S A. Aug. 30, 2011;108(35):14584-9. doi: 10.1073/pnas.1112188108. Epub Aug. 22, 2011.
Littman et al., Th17 and regulatory T cells in mediating and restraining inflammation. Cell. Mar. 19, 2010;140(6):845-58.
Lo et al., Molecular mimicry mediated by MHC class Ib molecules after infection with gram-negative pathogens. Nat Med. Feb. 2000;6(2):215-8.
Lo et al., T cell responses to Gram-negative intracellular bacterial pathogens: a role for CD8+ T cells in immunity to Salmonella infection and the involvement of MHC class Ib molecules. J Immunol. May 1, 1999;162(9):5398-406.
Lu et al., Induction of CD8+ regulatory T cells protects macaques against SIV challenge. Cell Rep. Dec. 27, 2012;2(6):1736-46. doi: 10.1016/j.celrep.2012.11.016. Epub Dec. 20, 2012.
Lu et al., Regulation of CD8+ regulatory T cells: Interruption of the NKG2A-Qa-1 interaction allows robust suppressive activity and resolution of autoimmune disease. Proc Natl Acad Sci U S A. Dec. 9, 2008;105(49):19420-5.
Martin et al., Defective CD95/APO-1/Fas signal complex formation in the human autoimmune lymphoproliferative syndrome, type Ia. Proc Natl Acad Sci U S A. Apr. 13, 1999;96(8):4552-7. Erratum in: Proc Natl Acad Sci U S A. May 18, 2004;101(20):7840.
Mestas et al., Of mice and not men: differences between mouse and human immunology. J Immunol. Mar. 1, 2004;172(5):2731-8.
Mingari et al., Human CD8+ T lymphocyte subsets that express HLA class I-specific inhibitory receptors represent oligoclonally or monoclonally expanded cell populations. Proc Natl Acad Sci U S A. Oct. 29, 1996;93(22):12433-8.
Mingari et al., Regulation of KIR expression in human T cells: a safety mechanism that may impair protective T-cell responses. Immunol Today. Apr. 1998;19(4):153-7.
Miyao et al., Plasticity of Foxp3(+) T cells reflects promiscuous Foxp3 expression in conventional T cells but not reprogramming of regulatory T cells. Immunity. Feb. 24, 2012;36(2):262-75. doi: 10.1016/j.immuni.2011.12.012. Epub Feb. 9, 2012.
Morel et al., Genetic reconstitution of systemic lupus erythematosus immunopathology with polycongenic murine strains. Proc Natl Acad Sci U S A. Jun. 6, 2000;97(12):6670-5.
Moretta et al., NK-CTLs, a novel HLA-E-restricted T-cell subset. Trends Immunol. Mar. 2003;24(3):136-43.
Moser et al., CD94-NKG2A receptors regulate antiviral CD8(+) T cell responses. Nat Immunol. Feb. 2002;3(2):189-95. Epub Jan. 22, 2002.
Mourmouras et al., Evaluation of tumour-infiltrating CD4+CD25+FOXP3+ regulatory T cells in human cutaneous benign and atypical naevi, melanomas and melanoma metastases. Br J Dermatol. Sep. 2007;157(3):531-9. Epub Jun. 26, 2007.
Nakagawa et al., Instability of Helios-deficient Tregs is associated with conversion to a T-effector phenotype and enhanced antitumor immunity. Proc Natl Acad Sci U S A. May 31, 2016;113(22):6248-53. doi: 10.1073/pnas.1604765113. Epub May 16, 2016.
O'Herrin et al., Antigen-specific blockade of T cells in vivo using dimeric MHC peptide. J Immunol. Sep. 1, 2001;167(5):2555-60.
Ohinata et al., Blimp1 is a critical determinant of the germ cell lineage in mice. Nature. Jul. 14, 2005;436(7048):207-13. Epub Jun. 5, 2005.
Ohkura et al., T cell receptor stimulation-induced epigenetic changes and Foxp3 expression are independent and complementary events required for Treg cell development. Immunity. Nov. 16, 2012;37(5):785-99. doi:10.1016/j.immuni.2012.09.010. Epub Nov. 1, 2012.
O'Shea et al., Genomic views of STAT function in CD4+ T helper cell differentiation. Nat Rev Immunol. Apr. 2011;11(4):239-50. doi: 10.1038/nri2958.
Panoutsakopoulou et al., Analysis of the relationship between viral infection and autoimmune disease. Immunity. Jul. 2001;15(1):137-47.

(56) References Cited

OTHER PUBLICATIONS

Park et al., Modulation of CD4+ T lymphocyte lineage outcomes with targeted, nanoparticle-mediated cytokine delivery. Mol Pharm. Feb. 7, 2011;8(1):143-52. doi: 10.1021/mp100203a. Epub Dec. 8, 2010.

Petrovas et al., SIV-specific CD8+ T cells express high levels of PD1 and cytokines but have impaired proliferative capacity in acute and chronic SIVmac251 infection. Blood. Aug. 1, 2007;110(3):928-36. Epub Apr. 17, 2007.

Pierson et al., Antiapoptotic Mcl-1 is critical for the survival and niche-filling capacity of Foxp3+ regulatory T cells. Nat Immunol. Sep. 2013;14(9):959-65. doi:10.1038/ni.2649. Epub Jul. 14, 2013.

Pietra et al., The analysis of the natural killer-like activity of human cytolytic T lymphocytes revealed HLA-E as a novel target for TCR alpha/beta-mediated recognition. Eur J Immunol. Dec. 2001;31(12):3687-93.

Pisitkun et al., Autoreactive B cell responses to RNA-related antigens due to TLR7 gene duplication. Science. Jun. 16, 2006;312(5780):1669-72. Epub May 18, 2006.

Platt et al., CRISPR-Cas9 knockin mice for genome editing and cancer modeling. Cell. Oct. 9, 2014;159(2):440-55. doi: 10.1016/j.cell.2014.09.014. Epub Sep. 25, 2014.

Roger et al., Cutting edge: Ly49A inhibits TCR/CD3-induced apoptosis and IL-2 secretion. J Immunol. Jul. 1, 2001;167(1):6-10.

Roy et al., Blimp-1 specifies neural crest and sensory neuron progenitors in the zebrafish embryo. Curr Biol. Oct. 5, 2004;14(19):1772-7.

Rubtsov et al., Stability of the regulatory T cell lineage in vivo. Science. Sep. 24, 2010;329(5999):1667-71. doi: 10.1126/science.1191996.

Rutishauser et al.,Transcriptional repressor Blimp-1 promotes CD8(+) T cell terminal differentiation and represses the acquisition of central memory T cell properties. Immunity. Aug. 21, 2009;31(2):296-308. doi:10.1016/j.immuni.2009.05.014. Epub Aug. 6, 2009.

Sakaguchi et al., Regulatory T cells and immune tolerance. Cell. May 30, 2008;133(5):775-87.

Sakuishi et al., Targeting Tim-3 and PD-1 pathways to reverse T cell exhaustion and restore anti-tumor immunity. J Exp Med. Sep. 27, 2010;207(10):2187-94. doi:10.1084/jem.20100643. Epub Sep. 6, 2010. Erratum in: J Exp Med. Jun. 6, 2011;208(6):1331.

Shin et al., A role for the transcriptional repressor Blimp-1 in CD8(+) T cell exhaustion during chronic viral infection. Immunity. Aug. 21, 2009;31(2):309-20. doi:10.1016/j.immuni.2009.06.019. Epub Aug. 6, 2009.

Slifka et al., Preferential escape of subdominant CD8+ T cells during negative selection results in an altered antiviral T cell hierarchy. J Immunol. Feb. 1, 2003;170(3):1231-9.

Soloski et al., Structural and functional characteristics of the class IB molecule, Qa-1. Immunol Rev. Oct. 1995;147:67-89.

Speiser et al., In vivo expression of natural killer cell inhibitory receptors by human melanoma-specific cytolytic T lymphocytes. J Exp Med. Sep. 20, 1999;190(6):775-82.

Subramanian et al., A Tlr7 translocation accelerates systemic autoimmunity in murine lupus. Proc Natl Acad Sci U S A. Jun. 27, 2006;103(26):9970-5. Epub Jun. 15, 2006.

Sugimoto et al., Foxp3-dependent and -independent molecules specific for CD25+CD4+ natural regulatory T cells revealed by DNA microarray analysis. Int Immunol. Aug. 2006;18(8):1197-209. Epub Jun. 13, 2006.

Sullivan et al., Positive selection of a Qa-1-restricted T cell receptor with specificity for insulin. Immunity. Jul. 2002;17(1):95-105.

Thornton et al., Expression of Helios, an Ikaros transcription factor family member, differentiates thymic-derived from peripherally induced Foxp3+ T regulatory cells. J Immunol. Apr. 1, 2010;184(7):3433-41.

Tompkins et al., Transporters associated with antigen processing (TAP)-independent presentation of soluble insulin to alpha/beta T cells by the class Ib gene product, Qa-1(b). J Exp Med. Sep. 7, 1998;188(5):961-71.

Transy et al., A low polymorphic mouse H-2 class I gene from the Tla complex is expressed in a broad variety of cell types. J Exp Med. Aug. 1, 1987;166(2):341-61.

Ugolini et al., Involvement of inhibitory NKRs in the survival of a subset of memory-phenotype CD8+ T cells. Nat Immunol. May 2001;2(5):430-5. Erratum in: Nat Immunol Jul. 2001;2(7):658.

Uniprot Submission; Accession No. P40933: Grabstein et al; Feb. 1, 1995; 2 pages.

Viguier et al., Foxp3 expressing CD4+CD25(high) regulatory T cells are overrepresented in human metastatic melanoma lymph nodes and inhibit the function of infiltrating T cells. J Immunol. Jul. 15, 2004;173(2):1444-53.

Vivier et al., Inhibitory NK-cell receptors on T cells: witness of the past, actors of the future. Nat Rev Immunol. Mar. 2004;4(3):190-8.

Wan et al., Regulatory T-cell functions are subverted and converted owing to attenuated Foxp3 expression. Nature. Feb. 15, 2007;445(7129):766-70. Epub Jan. 14, 2007.

Wang et al., CD8 regulatory T cells: what's old is now new. Immunol Cell Biol. Mar.-Apr. 2009;87(3):192-3. doi: 10.1038/icb.2009.8. Epub Feb. 24, 2009.

Wherry, T cell exhaustion. Nat Immunol. Jun. 2011;12(6):492-9.

Yamaguchi et al., Control of immune responses by antigen-specific regulatory T cells expressing the folate receptor. Immunity. Jul. 2007;27(1):145-59. Epub Jul. 5, 2007.

Yang et al., Opposing regulation of the locus encoding IL-17 through direct, reciprocal actions of STAT3 and STAT5. Nat Immunol. Mar. 2011;12(3):247-54. doi: 10.1038/ni.1995. Epub Jan. 30, 2011.

Yao et al., Nonredundant roles for Stat5a/b in directly regulating Foxp3. Blood. May 15, 2007;109(10):4368-75. Epub Jan. 16, 2007.

Yin et al., Ezh2 regulates differentiation and function of natural killer cells through histone methyltransferase activity. Proc Natl Acad Sci U S A. Dec. 29, 2015;112(52):15988-93. doi: 10.1073/pnas.1521740112. Epub Dec. 14, 2015.

Young et al., Differential expression of leukocyte receptor complex-encoded Ig-like receptors correlates with the transition from effector to memory CTL. J Immunol. Mar. 15, 2001;166(6):3933-41.

Zeng et al., Synergy of IL-21 and IL-15 in regulating CD8+ T cell expansion and function. J Exp Med. Jan. 3, 2005;201(1):139-48.

Zhang et al., Potent and selective stimulation of memory-phenotype CD8+ T cells in vivo by IL 15. Immunity. May 1998;8(5):591-9.

Zhu et al., The Tim-3 ligand galectin-9 negatively regulates T helper type 1 immunity. Nat Immunol. Dec. 2005;6(12):1245-52. Epub Nov. 13, 2005.

Zorn et al., IL-2 regulates FOXP3 expression in human CD4+CD25+ regulatory T cells through a STAT-dependent mechanism and induces the expansion of these cells in vivo. Blood. Sep. 1, 2006;108(5):1571-9. Epub Apr. 27, 2006.

Zou, Regulatory T cells, tumour immunity and immunotherapy. Nat Rev Immunol. Apr. 2006;6(4):295-307.

International Preliminary Report on Patentability for PCT/US2016/035692 dated Dec. 14, 2017.

Baumeister et al., Coinhibitory Pathways in Immunotherapy for Cancer.Annu Rev Immunol. May 20, 2016;34:539-73. doi: 10.1146/annurev-immunol-032414-112049. Epub Feb. 25, 2016.

Chauvin et al., TIGIT and PD-1 impair tumor antigen-specific CD8+ T cells in melanoma patients J Clin Invest. May 2015;125(5):2046-58. doi: 10.1172/JCI80445. Epub Apr. 13, 2015.

Coussens et al., Inflammation and cancer. Nature. Dec. 19-26, 2002;420(6917):860-7.

Franciso et al., PD-L1 regulates the development, maintenance, and function of induced regulatory T cells. J Exp Med. Dec. 21, 2009;206(13):3015-29. doi: 10.1084/jem.20090847. Epub Dec. 14, 2009.

Hirschhorn-Cymerman et al., Induction of tumoricidal function in CD4+ T cells is associated with concomitant memory and terminally differentiated phenotype. J Exp Med. Oct. 22, 2012;209(11):2113-26. doi: 10.1084/jem.20120532. Epub Sep. 24, 2012.

Kurtulus et al., TIGIT predominantly regulates the immune response via regulatory T cells. J Clin Invest. Nov. 2, 2015;125(11):4053-62. doi: 10.1172/JCI81187. Epub Sep. 28, 2015.

Liston et al., Homeostatic control of regulatory T cell diversity. Nat Rev Immunol. Mar. 2014;14(3):154-65. doi: 10.1038/nri3605. Epub Jan. 31, 2014.

(56) References Cited

OTHER PUBLICATIONS

Mahoney et al., Combination cancer immunotherapy and new immunomodulatory targets. Nat Rev Drug Discov. Aug. 2015;14(8):561-84. doi: 10.1038/nrd4591.
Malandro et al., Clonal Abundance of Tumor-Specific CD4(+) T Cells Potentiates Efficacy and Alters Susceptibility to Exhaustion. Immunity. Jan. 19, 2016;44(1):179-193. doi: 10.1016/j.immuni.2015.12.018.
Malchow et al., Aire-dependent thymic development of tumor-associated regulatory T cells. Science. Mar. 8, 2013;339(6124):1219-24. doi: 10.1126/science.1233913.
Murphy et al., Anaphylaxis caused by repetitive doses of a GITR agonist monoclonal antibody in mice. Blood. Apr. 3, 2014;123(14):2172-80. doi: 10.1182/blood-2013-12-544742. Epub Feb. 20, 2014.
Ngiow et al., Anti-TIM3 antibody promotes T cell IFN-γ-mediated antitumor immunity and suppresses established tumors. Cancer Res. May 15, 2011;71(10):3540-51. doi: 10.1158/0008-5472.CAN-11-0096. Epub Mar. 23, 2011.
Nishikawa et al., Regulatory T cells in cancer immunotherapy. Curr Opin Immunol. Apr. 2014;27:1-7. doi: 10.1016/j.coi.2013.12.005. Epub Jan. 14, 2014.
Page et al., Immune modulation in cancer with antibodies. Annu Rev Med. 2014;65:185-202. doi: 10.1146/annurev-med-092012-112807. Epub Oct. 30, 2013.
Pardoll, The blockade of immune checkpoints in cancer immunotherapy. Nat Rev Cancer. Mar. 22, 2012;12(4):252-64. doi: 10.1038/nrc3239.
Quezada et al., Tumor-reactive CD4(+) T cells develop cytotoxic activity and eradicate large established melanoma after transfer into lymphopenic hosts. J Exp Med. Mar. 15, 2010;207(3):637-50. doi: 10.1084/jem.20091918. Epub Feb. 15, 2010.
Sakuishi et al., TIM3+FOXP3+ regulatory T cells are tissue-specific promoters of T-cell dysfunction in cancer. Oncoimmunology. Apr. 1, 2013;2(4):e23849.
Scanlan et al., Cancer/testis antigens: an expanding family of targets for cancer immunotherapy. Immunol Rev. Oct. 2002;188:22-32.
Schaer et al., GITR pathway activation abrogates tumor immune suppression through loss of regulatory T cell lineage stability. Cancer Immunol Res. Nov. 2013;1(5):320-31. doi: 10.1158/2326-6066.CIR-13-0086.
Sebastian et al., Helios Controls a Limited Subset of Regulatory T Cell Functions. J Immunol. Jan. 1, 2016;196(1):144-55. doi: 10.4049/jimmunol.1501704. Epub Nov. 18, 2015.
Shimizu et al., Stimulation of CD25(+)CD4(+) regulatory T cells through GITR breaks immunological self-tolerance. Nat Immunol. Feb. 2002;3(2):135-42. Epub Jan. 22, 2002.
Simpson et al., Fc-dependent depletion of tumor-infiltrating regulatory T cells co-defines the efficacy of anti-CTLA-4 therapy against melanoma. J Exp Med. Aug. 26, 2013;210(9):1695-710. doi: 10.1084/jem.20130579. Epub Jul. 29, 2013.
Sugiyama et al., Anti-CCR4 mAb selectively depletes effector-type FoxP3+CD4+ regulatory T cells, evoking antitumor immune responses in humans. Proc Natl Acad Sci U S A. Oct. 29, 2013;110(44):17945-50. doi: 10.1073/pnas.1316796110. Epub Oct. 14, 2013.
Xiao et al., GITR subverts Foxp3+ Tregs to boost Th9 immunity through regulation of histone acetylation. Nature Communications. Sep. 14, 2015;6:8266.
Extended European Search Report for Application No. EP1680451.4 dated Dec. 20, 2018.
International Search Report and Written Opinion for PCT/US2015/047189 dated Feb. 2, 2016.
International Preliminary Report on Patentability for PCT/US2015/047189 dated Mar. 9, 2017.
Partial Supplementary European Search Report for EP 15836839.9 dated Jan. 11, 2018.
Extended European Search Report for Application No. EP 15836839.9 dated Apr. 11, 2018.
[No Author Listed], Peripheral blood mononuclear cell From Wikipedia, the free encyclopedia; pp. 1-2 downloaded on Jul. 13, 2018.

Alvarez et al., Disruption of CD8+ Treg activity results in expansion of T follicular helper cells and enhanced antitumor immunity. Cancer Immunol Res. Mar. 2014;2(3):207-16. doi: 10.1158/2326-6066.CIR-13-0121. Epub Dec. 31, 2013.
Aoki et al., Fluorescence resonance energy transfer imaging of cell signaling from in vitro to in vivo: basis of biosensor construction, live imaging, and image processing. Dev Growth Differ. May 2013;55(4):515-22. doi:10.1111/dgd.12039. Epub Feb. 7, 2013.
Arai et al., Extensive use of FRET in biological imaging. Microscopy (Oxf). Aug. 2013;62(4):419-28.
Aramburu et al., Affinity-driven peptide selection of an NFAT inhibitor more selective than cyclosporin A. Science. Sep. 24, 1999;285(5436):2129-33.
Ashkar et al., Eta-1 (osteopontin): an early component of type-1 (cell-mediated) immunity. Science. Feb. 4, 2000;287(5454):860-4.
Baine et al., Helios induces epigenetic silencing of IL2 gene expression in regulatory T cells. J Immunol. Feb. 1, 2013;190(3):1008-16. doi: 10.4049/jimmunol.1200792. Epub Dec. 28, 2012.
Baumjohann et al., Identification of T follicular helper (Tfh) cells by flow cytometry. Protocal Exchange. Jun. 18, 2013.
Baumjohann et al., Cutting Edge: Distinct waves of BCL6 expression during T follicular helper cell development. J Immunol. Sep. 1, 2011;187(5):2089-92. doi: 10.4049/jimmunol.1101393. Epub Jul. 29, 2011.
Beerens et al., Protein transduction domains and their utility in gene therapy. Curr Gene Ther. Oct. 2003;3(5):486-94.
Bindea et al., Spatiotemporal dynamics of intratumoral immune cells reveal the immune landscape in human cancer. Immunity. Oct. 17, 2013;39(4):782-95. doi: 10.1016/j.immuni.2013.10.003.
Broomé et al., Primary sclerosing cholangitis, inflammatory bowel disease, and colon cancer. Semin Liver Dis. Feb. 2006;26(1):31-41.
Buback et al., Osteopontin and the skin: multiple emerging roles in cutaneous biology and pathology. Exper. Dermatol. 2009;18:750-759.
Bunting et al., New effector functions and regulatory mechanisms of BCL6 in normal and malignant lymphocytes. Curr Opin Immunol. Jun. 2013;25(3):339-46. Doi:10.1016/j.coi.2013.05.003. Epub May 30, 2013.
Buommino et al., Osteopontin: a new emerging role in psoriasis. Arch. Dermatol. Res. 2009;301:397-404.
Cantor et al., Regulation of T-helper-cell lineage development by osteopontin: the inside story. Nat Rev Immunol. Feb. 2009;9(2):137-41. Doi:10.1038/nri2460.
Carbone et al., Report of the Committee on Hodgkin's Disease Staging Classification. Cancer Res. Nov. 1971;31(11):1860-1.
Cerchietti et al., A purine scaffold Hsp90 inhibitor destabilizes BCL-6 and has specific antitumor activity in BCL-6-dependent B cell lymphomas. Nat Med. Dec. 2009;15(12):1369-76. Doi: 10.1038/nm.2059. Epub Nov. 22, 2009.
Chagan-Yasutan et al., Involvement of osteopontin and its signaling molecule CD44 in clinicopathological features of adult T cell leukemia. Leukemia Res. May 9, 2011;35(11):1484-90.
Chang et al., TRAF3 regulates the effector function of regulatory T cells and humoral immune responses. J Exp Med. Jan. 13, 2014;211(1):137-51. Doi:10.1084/jem.20131019. Epub Dec. 30, 2013.
Chen et al., Elevated plasma osteopontin level is associated with occurrence of psoriasis and is an unfavorable cardiovascular risk factor in patients with psoriasis. J Am Acad Dermatol. Feb. 2009;60(2):225-30. Doi: 10.1016/j.jaad.2008.09.046. Epub Nov. 25, 2008.
Choi et al., Cutting edge: STAT1 is required for IL-6-mediated Bcl6 induction for early follicular helper cell differentiation. J Immunol. Apr. 1, 2013;190(7):3049-53. Doi:10.4049/jimmunol.1203032. Epub Feb. 27, 2013.
Choi et al., ICOS receptor instructs T follicular helper cell versus effector cell differentiation via induction of the transcriptional repressor Bcl6. Immunity. Jun. 24, 2011;34(6):932-46. Doi: 10.1016/j.immuni.2011.03.023.
Chung et al., Follicular regulatory T (Tfr) cells with dual Foxp3 and Bcl6 expression suppress germinal center reactions. Nat Med. Jul. 24, 2011;17(8):983-8. Doi: 10.1038/nm.2426.

(56) References Cited

OTHER PUBLICATIONS

Compston et al., Multiple sclerosis. Lancet. Oct. 25, 2008;372(9648):1502-17. Doi: 10.1016/S0140-6736(08)61620-7.
Crotty et al., Effectors and memories: Bcl-6 and Blimp-1 in T and B lymphocyte differentiation. Nat Immunol. Feb. 2010;11(2):114-20. Doi: 10.1038/ni.1837. Epub Jan. 19, 2010.
Crotty, Follicular helper CD4 T cells (TFH). Annu Rev Immunol. 2011;29:621-63. Doi: 10.1146/annurev-immunol-031210-101400.
Deshayes et al., Fluorescence technologies for monitoring interactions between biological molecules in vitro. Prog Mol Biol Transl Sci. 2013;113:109-43. Doi: 10.1016/B978-0-12-386932-6.00004-1.
Diamandis et al., The biotin-(strept)avidin system: principles and applications in biotechnology. Clin Chem. May 1991;37(5):625-36.
Doria et al., Long-term prognosis and causes of death in systemic lupus erythematosus. Am J Med. Aug. 2006;119(8):700-6.
Duk et al., The biotin/avidin-mediated microtiter plate lectin assay with the use of chemically modified glycoprotein ligand. Anal Biochem. Sep. 1994;221(2):266-72.
Gandhi et al., Are patients with inflammatory bowel disease at increased risk of coronary artery disease? Am J Med. Oct. 2012;125(10):956-62. Doi: 10.1016/j.amjmed.2012.03.015. Epub Jul. 25, 2012.
Gigoux et al., Inducible costimulatory promotes helper T-cell differentiation through phosphoinositide 3-kinase. Proc Natl Acad Sci U S AA. Dec. 1, 2009;106(48):20371-6. Doi:10.1073/pnas.0911573106. Epub Nov. 13, 2009.
Glasmacher et al., Roquin binds inducible ignaling ory Mrna and effectors of Mrna decay to induce microRNA-independent post-transcriptional repression. Nat Immunol. Aug. 2010;11(8):725-33. Doi: 10.1038/ni.1902. Epub Jul. 18, 2010.
Goedhart et al., An introduction to fluorescence imaging techniques geared towards biosensor applications. Methods Mol Biol. 2014;1071:17-28. Doi: 10.1007/978-1-62703-622-1_2.
Haxhinasto et al., The AKT-Mtor axis regulates de novo differentiation of CD4+Foxp3+ cells. J Exp Med. Mar. 17, 2008;205(3):565-74. Doi:10.1084/jem.20071477. Epub Feb. 18, 2008.
Hedfors et al., Long-term proliferation and survival of in vitro-activated T cells is dependent on Interleukin-2 receptor Signaling but not on the high-affinity IL-2R. Scand J Immunol. Nov. 2003;58(5):522-32.
Hirsch et al., Easily reversible desthiobiotin binding to streptavidin, avidin, and other biotin-binding proteins: uses for protein labeling, detection, and isolation. Anal Biochem. Sep. 15, 2002;308(2):343-57.
Huang et al., Gene expression profiles in BCL11B-siRNA treated malignant T cells. J. Hermatol Oncol. May 15, 2011;4(1, 23):1-6.
Huang et al., Lineage-specific functions of Bcl-6 in immunity and inflammation are mediated by distinct biochemical mechanisms. Nat Immunol. Apr. 2013;14(4):380-8. Doi: 10.1038/ni.2543. Epub Mar. 3, 2013.
Huff et al., A fluorescent glutathione analog for monitoring interactions of GST fusion proteins. The FASEB Journal. Apr. 2012;26(1):613.6.
Hur et al., Osteopontin-induced relapse and progression of autoimmune brain disease through enhanced survival of activated T cells. Nat Immunol. Jan. 2007;8(1):74-83. Epub Dec. 3, 2006.
Iaffaldano et al., The improvement of cognitive functions is associated with a decrease of plasma Osteopontin levels in Natalizumab treated relapsing multiple sclerosis. Brain Behav Immun Jan. 2014;35:176-81. Doi: 10.1016/j.bbi.2013.08.009. Epub Aug. 30, 2013.
Inoue et al., Intracellular osteopontin (iOPN) and immunity. Immunol Res. Apr. 2011;49(1-3):160-72. Doi: 10.1007/s12026-010-8179-5.
Jiang et al. HLA-E-restricted regulatory CD8(+) T cells are involved in development and control of human autoimmune type 1 diabetes. J Clin Invest. Oct. 2010;120(10):3641-50. doi: 10.1172/JCI43522. Epub Sep. 27, 2010.

Johnston et al., Bcl6 and Blimp-1 are reciprocal and antagonistic regulators of T follicular helper cell differentiation. Science. Aug. 21, 2009;325(5943):1006-10. Doi: 10.1126/science.1175870. Epub Jul. 16, 2009.
June, Principles of adoptive T cell cancer therapy. J Clin Invest. May 2007;117(5):1204-12.
Kaleta, Role of Osteopontin in Systemic Lupus Erythematosus. Arch Immunol. Ther. Exp. 2014;62:475-482.
Kalos et al., Adoptive T cell transfer for cancer immunotherapy in the era of synthetic biology. Immunity. Jul. 25, 2013;39(1):49-60. doi:10.1016/j.immuni.2013.07.002.
Kaluza et al., Improving the outcome of adoptive cell transfer by targeting tumor escape. Oncoimmunollogy. Jan. 2013;2(1):e22059-1-3.
Kang et al., MicroRNAs of the miR-17~92 family are critical regulators of T(FH) differentiation. Nat Immunol. Aug. 2013;14(8):849-57. doi: 10.1038/ni.2648. Epub Jun. 30, 2013.
Karttunen et al., Detection of rare antigen-presenting cells by the lacZ T-cell activation assay suggests an expression cloning strategy for T-cell antigens. Proc Natl Acad Sci U S A. Jul. 1, 1992;89(13):6020-4.
Kerfoot et al., Germinal center B cell and T follicular helper cell development initiates in the interfollicular zone. Immunity. Jun. 24, 2011;34(6):947-60. doi:10.1016/j.immuni.2011.03.024.
Keszei et al., Expansion of an osteopontin-expressing T follicular helper cell subset correlates with autoimmunity in B6.Sle1b mice and is suppressed by the H1-isoform of the Slamf6 receptor. FASEB J. Aug. 2013;27(8):3123-31. doi: 10.1096/fj.12-226951. Epub Apr. 29, 2013.
Kim et al., Inhibition of follicular T-helper cells by CD8(+) Treg is essential for self tolerance. Nature. Sep. 16, 2010;467(7313):328-32. doi: 10.1038/nature09370.
King et al., T follicular helper (TFH) cells in normal and dysregulated immune responses. Annu Rev Immunol. 2008;26:741-66. doi:10.1146/annurev.immunol.26.021607.090344.
Krönke et al., Lenalidomide causes selective degradation of IKZF1 and IKZF3 in multiple myeloma cells. Science. Jan. 17, 2014;343(6168):301-5. doi:10.1126/science.1244851. Epub Nov. 29, 2013.
Lampe et al., Polyclonal B cell activation by the Eta-1 cytokine and the development of systemic autoimmune disease. J Immunol. Nov. 1, 1991;147(9):2902-6.
Lang et al., Asthma severity in childhood, untangling clinical phenotypes. Pediatr Allergy Immunol. Sep. 2010;21(6):945-53. doi: 10.1111/j.1399-3038.2010.01072.x.
Leavenworth et al., A p85α-osteopontin axis couples the receptor ICOS to sustained Bcl-6 expression by follicular helper and regulatory T cells. Nat Immunol. Jan. 2015;16(1):96-106. doi: 10.1038/ni.3050. Epub Dec. 1, 2014.
Leavenworth et al., Amelioration of arthritis through mobilization of peptide-specific CD8+ regulatory T cells. J Clin Invest. Mar. 2013;123(3):1382-9. doi: 10.1172/JCI66938. Epub Feb. 8, 2013.
Lequin, Enzyme immunoassay (EIA)/enzyme-linked immunosorbent assay (ELISA). Clin Chem. Dec. 2005;51(12):2415-8. Epub Sep. 22, 2005.
Lim et al., Parkin mediates nonclassical, proteasomal-independent ubiquitination of synphilin-1: implications for Lewy body formation. J Neurosci. Feb. 23, 2005;25(8):2002-9.
Lindqvist et al., Prognostic laboratory markers of joint damage in rheumatoid arthritis. Ann Rheum Dis. Feb. 2005;64(2):196-201. Epub Sep. 30, 2004.
Linterman et al., Foxp3+ follicular regulatory T cells control T follicular helper cells and the germinal center reponse. Nat Med. Jul. 24, 2011;17(8):975-82. doi: 10.1038/nm.2425.
Lister et al., Report of a committee convened to discuss the evaluation and staging of patients with Hodgkin's disease: Cotswolds meeting. J Clin Oncol. Nov. 1989;7(11):1630-6. Erratum in: J Clin Oncol Sep. 1990;8(9):1602.
Lublin et al., Defining the clinical course of multiple sclerosis: results of an international survey. National Multiple Sclerosis Society (USA) Advisory Committee on Clinical Trials of New Agents in Multiple Sclerosis. Neurology. Apr. 1996;46(4):907-11.

(56) References Cited

OTHER PUBLICATIONS

Ma et al., Human T follicular helper (Tfh) cells and disease. Immunol Cell Biol. Jan. 2014;92(1):64-71. doi: 10.1038/icb.2013. 55. Epub Oct. 22, 2013.
Ma et al., The origins, function, and regulation of T follicular helper cells. J Exp Med. Jul. 2, 2012;209(7):1241-53. doi:10.1084/jem. 20120994.
Medeiros et al., Anaplastic Large Cell Lymphoma. Am J Clin Pathol. May 2007;127(5):707-22.
Miller et al., Clinically isolated syndromes suggestive of multiple sclerosis, part I: natural history, pathogenesis, diagnosis, and prognosis. Lancet Neurol. May 2005;4(5):281-8.
Mishima et al., High plasma osteopontin levels in patients with inflammatory bowel disease. J Clin Gastroenterol. Feb. 2007;41(2):167-72.
Modesti, Fluorescent labeling of proteins. Methods Mol Biol. 2011;783:101-20. doi: 10.1007/978-1-61779-282-3_6.
Mok et al., A prospective study of survival and prognostic indicators of systemic lupus erythematosus in a southern Chinese population. Rheumatology (Oxford). Apr. 2000;39(4):399-406.
Mrowietz et al., Definition of treatment goals for moderate to severe psoriasis: a European consensus. Arch Dermatol Res. Jan. 2011;303(1):1-10. doi: 10.1007/s00403-010-1080-1. Epub Sep. 21, 2010.
Münst et al., Engineering cell-permeable protein. J Vis Exp. Dec. 28, 2009;(34). pii: 1627. doi: 10.3791/1627.
Nahar, Covalent immobilization of proteins onto photo activated polystyrene microtiter plates for enzyme-linked immunosorbent assay procedures. Protocol Exchange Dec. 5, 2013.
Nakase et al., Overexpression of novel short isoforms of Helios in a patient with T-cell acute lymphoblastic leukemia. Exp Hematol. Apr. 2002;30(4):313-7.
Nakayamada et al.,Type I IFN induces binding of STAT1 to Bcl6: divergent roles of STAT family transcription factors in the T follicular helper cell genetic program. J Immunol. Mar. 1, 2014;192(5):2156-66. doi: 10.4049/jimmunol.1300675. Epub Jan. 31, 2014.
Nurieva et al., Bcl6 mediates the development of T follicular helper cells. Science. Aug. 21, 2009;325(5943):1001-5. doi: 10.1126/science.1176676. Epub Jul. 23, 2009.
Obenauer et al., Scansite 2.0: Proteome-wide prediction of cell signaling interactions using short sequence motifs. Nucleic Acids Res. Jul. 1, 2003;31(13):3635-41.
Park et al., The regulatory subunits of PI3K, p85alpha and p85beta, interact with XBP-1 and increase its nuclear translocation. Nat Med. Apr. 2010;16(4):429-37. doi: 10.1038/nm.2099. Epub Mar. 28, 2010.
Patarca et al., Differential induction of interferon gamma gene expression after activation of CD4+ T cells by conventional antigen and Mls superantigen. Proc Natl Acad Sci U S A. Apr. 1, 1991;88(7):2736-9.
Patarca et al., Dysregulated expression of the T cell cytokine Eta-1 in CD4-8-lymphocytes during the development of murine autoimmune disease. J Exp Med. Oct. 1, 1990;172(4):1177-83.
Pedersen et al., Development of assay platforms for in vitro screening of Treg modulating potential of pharmacological compounds. Immunopharmacol Immunotoxicol. Feb. 2015;37(1):63-71. doi: 10.3109/08923973.2014.977449. Epub Nov. 4, 2014.
Polo et al., Specific peptide interference reveals BCL6 transcriptional and oncogenic mechanisms in B-cell lymphoma cells. Nat Med. Dec. 2004;10(12):1329-35. Epub Nov. 7, 2004.
Powell et al., Expression profiling of a hemopoietic cell survival transcriptome implicates osteopontin as a functional prognostic factor in AML. Blood. Nov. 26, 2009;114(23):4859-70. doi:10.1182/blood-2009-02-204818. Epub Oct. 5, 2009.
Roifman et al., Evidence of endothelial dysfunction in patients with inflammatory bowel disease. Clin Gastroenterol Hepatol. Feb. 2009;7(2):175-82. doi: 10.1016/j.cgh.2008.10.021. Epub Oct. 30, 2008.
Rojas et al., Genetic engineering of proteins with cell membrane permeability. Nat Biotechnol. Apr. 1998;16(4):370-5.

Rolf et al., Phosphoinositide 3-kinase activity in T cells regulates the magnitude of the germinal center reaction. J Immunol. Oct. 1, 2010;185(7):4042-52. doi: 10.4049/jimmunol.1001730. Epub Sep. 8, 2010.
Rolf et al., Signaling pathways in T follicular helper cells. J Immunol. Jun. 15, 2010;184(12):6563-8. doi: 10.4049/jimmunol. 1000202.
Rullo et al., Plasma levels of osteopontin identify patients at risk for organ damage in systemic lupus erythematosus. Arthritis Res Ther. Jan. 23, 2013;15(1):R18. doi: 10.1186/ar4150.
Sage et al., PD-1 controls Lymph Node and Blood T Follicular Regulatory Cells. Nat Immunol. Feb. 2013;14(2):152-61. doi: 10.1038/ni.2496. Epub Dec. 16, 2012.
Samitas et al., Osteopontin expression and relation to disease severity in human asthma. Eur Respir J. Feb. 2011;37(2):331-41. doi: 10.1183/09031936.00017810. Epub Jun. 18, 2010.
Sasaki et al., Function of PI3Kgamma in thymocyte development, T cell activation, and neutrophil migration. Science. Feb. 11, 2000;287(5455):1040-6.
Sato et al., Osteopontin/Eta-1 upregulated in Crohn's disease regulates theTh1 immune response. Gut. Sep. 2005;54(9):1254-62.
Schafer et al., Microglia sculpt postnatal neural circuits in an activity and complement-dependent manner. Neuron. May 24, 2012;74(4):691-705. doi: 10.1016/j.neuron.2012.03.026.
Shinohara et al., Alternative translation of osteopontin generates intracellular and secreted isoforms that mediate distinct biological activities in dendritic cells. Proc Natl Acad Sci U S A. May 20, 2008;105(20):7235-9. doi: 10.1073/pnas.0802301105. Epub May 14, 2008.
Shinohara et al., Engagement of the type I interferon receptor on dendritic cells inhibits T helper 17 cell development: role of intracellular osteopontin. Immunity. Jul. 18, 2008;29(1):68-78. doi:10. 1016/j.immuni.2008.05.008.
Shinohara et al., T-bet-dependent expression of osteopontin contributes to T cell polarization. Proc Natl Acad Sci U S A. Nov. 22, 2005;102(47):17101-6. Epub Nov. 14, 2005.
Tafuri et al., ICOS is essential for effective T-helper-cell responses. Nature. Jan. 4, 2001;409(6816):105-9.
Takahashi et al., Role of ERas in promoting tumour-like properties in mouse embryonic stem cells. Nature. May 29, 2003;423(6939):541-5.
Tarner et al., Treatment of autoimmune disease by adoptive cellular gene therapy. Ann N Y Acad Sci. Sep. 2003;998:512-9.
Tey et al., Adoptive T-cell transfer in cancer immunotherapy. Immunol Cell Biol. Jun. 2006;84(3):281-9.
Thompson et al., Prognosis and prognostic factors in inflammatory bowel disease. Saudi J Gastroenterol. Sep. 1995;1(3):129-37.
Tsang et al., Multiple sclerosis—diagnosis, management and prognosis. Aust Fam Physician. Dec. 2011;40(12):948-55.
Tun et al., Pathway analysis of primary central nervous system lymphoma. Blood. Mar. 15, 2008;111(6):3200-10. doi: 10.1182/blood-2007-10-119099. Epub Jan. 9, 2008.
Uede et al., Osteopontin, intrinsic tissue regulator of intractable inflammatory diseases. Pathol. Int. 2011;61:265-280.
Van Den Berg et al., Protein transduction domain delivery of therapeutic macromolecules. Curr Opin Biotechnol. Dec. 2011;22(6):888-93. doi:10.1016/j.copbio.2011.03.008. Epub Apr. 12, 2011.
Vinuesa et al., A RING-type ubiquitin ligase family member required to repress follicular helper T cells and autoimmunity. Nature. May 26, 2005;435(7041):452-8.
Wadia et al., Transducible TAT-HA fusogenic peptide enhances escape of TAT-fusion proteins after lipid raft macropinocytosis. Nat Med. Mar. 2004;10(3):310-5. Epub Feb. 8, 2004.
Weinmayr et al., Asthma phenotypes identified by latent class analysis in the ISAAC phase II Spain study. Clin Exp Allergy. Feb. 2013;43(2):223-32. doi: 10.1111/cea.12035.
Wieczorek et al., Genetically modified T cells for the treatment of malignant disease. Transfus Med Hemother. Dec. 2013;40(6):388-402. doi:10.1159/000357163. Epub Nov. 29, 2013.

(56) References Cited

OTHER PUBLICATIONS

Winnay et al., A Novel Interaction Between the Regulatory Subunit of PI 3-Kinase and X-box Binding Portein-1 Modulates the Unfolded Protein Response. Nat Med. Apr. 2010;16(4):438-45. doi: 10.1038/nm.2121. Epub Mar. 28, 2010.
Wong et al., Elevation of plasma osteopontin concentration is correlated with disease activity in patients with systemic lupus erythematosus. Rheumatology (Oxford). May 2005;44(5):602-6. Epub Feb. 10, 2005.
Xu et al., Follicular T-helper cell recruitment governed by bystander B cells and ICOS-driven motility. Nature. Apr. 25, 2013;496(7446):523-7. doi:10.1038/nature12058.
Yaffe et al., A motif-based profile scanning approach for genome-wide prediction of signaling pathways. Nat Biotechnol. Apr. 2001;19(4):348-53.
Yaffe et al., The structural basis for 14-3-3:phosphopeptide binding specificity. Cell. Dec. 26, 1997;91(7):961-71.
Yawn, Factors accounting for asthma variability: achieving optimal symptom control for individual patients. Prim Care Respir J. Sep. 2008;17(3):138-47. doi: 10.3132/pcrj.2008.00004.
Yu et al., Roquin represses autoimmunity by limiting inducible T-cell co-stimulator messenger RNA. Nature. Nov. 8, 2007;450(7167):299-303. doi: 10.1038/nature06253. Erratum in: Nature. Feb. 21, 2008;451(7181):1022.
Yu et al., The transcriptional repressor Bcl-6 directs T follicular helper cell lineage commitment. Immunity. Sep. 18, 2009;31(3):457-68. doi:10.1016/j.immuni.2009.07.002. Epub Jul. 23, 2009.
Yu et al.., Regulation of the p85/p110 phosphatidylinositol 3'-kinase: stabilization and inhibition of the p110alpha catalytic subunit by the p85 regulatory subunit. Mol Cell Biol. Mar. 1998;18(3):1379-87.
Zeug et al., Quantitative intensity-based FRET approaches—a comparative snapshot. Biophys J. Nov. 7, 2012;103(9):1821-7. doi:10.1016/j.bpj.2012.09.031.
Zhao et al., The oncogenic properties of mutant p110alpha and p110beta phosphatidylinositol 3-kinases in human mammary epithelial cells. Proc Natl Acad Sci U S A. Dec. 20, 2005;102(51):18443-8. Epub Dec. 8, 2005.

U.S. Appl. No. 13/878,894, filed Jun. 26, 2013, Published, 2013-0302276.
U.S. Appl. No. 14/431,113, filed Mar. 25, 2015, Published, 2015-0250862.
EP11835009.9, Jan. 12, 2015, Partial Supplementary European Search Report.
EP 11835009.9, May 13, 2015, Extended European Search Report.
EP 11835009.9, Jun. 19, 2015, Corrected European Search Opinion.
PCT/US2011/056746, Feb. 21, 2012, Invitation to Pay Additional Fees.
PCT/US2011/056746, May 1, 2012, International Search Report and Written Opinion.
PCT/US2011/056746, May 2, 2013, International Preliminary Report on Patentability.
PCT/US2013/061851, Jan. 31, 2014, Invitation to Pay Additional Fees.
PCT/US2013/061851, Apr. 10, 2014, International Search Report and Written Opinion.
PCT/US2013/061851, Jun. 25, 2015, International Preliminary Report on Patentability.
PCT/US2016/035692, Sep. 13, 2016, International Search Report and Written Opinion.
U.S. Appl. No. 15/578,871, filed Dec. 1, 2017, Pending.
PCT/US2016/035692, Dec. 5, 2017, International Preliminary Report on Patentability.
U.S. Appl. No. 13/878,894, filed Jun. 26, 2013, Abandoned, 2013-0302276.
U.S. Appl. No. 15/506,868, filed Feb. 27, 2017, Abandoned, 2017-0269076.
U.S. Appl. No. 16/195,586, filed Nov. 19, 2018, Pending.
EP1680451.4, Dec. 20, 2018, Extended European Search Report.
PCT/US2015/047189, Feb. 2, 2016, International Search Report and the Written Opinion.
PCT/US2015/047189, Mar. 9, 2017, International Preliminary Report on Patentability.
EP 15836839.9, Jan. 11, 2018, Partial Supplementary European Search Report.
EP 15836839.9, Apr. 11, 2018, Extended European Search Report.

* cited by examiner

Suppressive activity of CD44+CD122+ CD8+ T cells: High affinity anti-NP response Qa-1 dependent suppression of autoantibody response

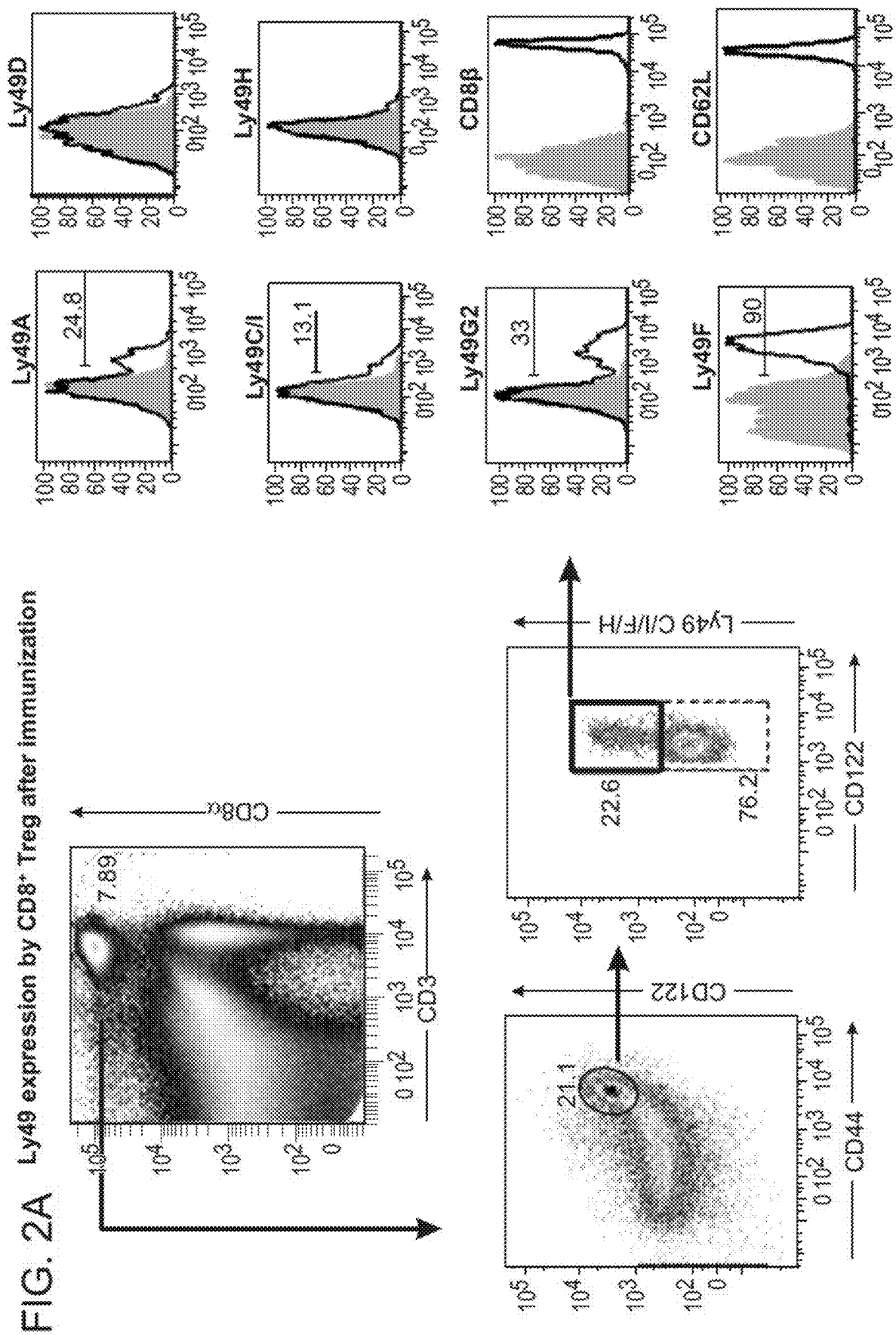

CD44⁺CD122⁺Ly49⁺ CD8 T cells account for Qa-1 restricted suppressive activity

Increased number of $T_{FH}$ and GC B cells in B6.Yaa mice

Impaired suppressive activity of CD8+ T cells from B6-Yaa mice

High affinity anti-NP Ab response

Total anti-NP Ab response

High affinity anti-NP Ab response

Fig. 6

NCBI Reference Sequence: NP_000576.1 (Human Il-15): SEQ ID NO: 1 mriskphlrs isiqcylcll lnshflteag ihvfilgcfs aglpkteanw vnvisdlkki
edliqsmhid atlytesdvh psckvtamkc fllelqvisl esgdasihdt venliilann
slssngnvte sgckeceele eknikeflqs fvhivqmfin ts Comparison of survival of C57BL/6 Qa-1(D227K) knock in mice with C57BL/6 mice after vaccination with irradiated B16-GM-CSF-transduced cells (1,2) one week before subcutaneous challenge with $5 \times 10^5$ B16 cells in opposite flank.

Helios expression by Ly49+ CD8 Treg

Innate receptors are highly upregulated in Ly49+ CD8+ T cells

Increase of activated CD4 and CD8 T cells in recipients of Helios KO BM

In vivo suppression: impaired suppressive activity of Helios deficient CD8+ T cells

DISCOVERY OF REGULATORY T CELLS PROGRAMMED TO SUPPRESS AN IMMUNE RESPONSE

RELATED APPLICATIONS

This application is a divisional of U.S. application Ser. No. 13/878,894 now abandoned, which was filed on Jun. 26, 2013 and which is a national stage filing under 35 U.S.C. § 371 of international application PCT/US2011/056746, which was filed on Oct. 18, 2011 and published under PCT Article 21(2) in English, and which claims the benefit under 35 U.S.C. § 119(e) of U.S. provisional application Ser. No. 61/405,696, filed Oct. 22, 2010, the content of each referenced application is incorporated by reference herein in its entirety.

FEDERALLY SPONSORED RESEARCH

This invention was made with government support under grant number A1037562 awarded by The National Institutes of Health. The government has certain rights in the invention.

BACKGROUND OF THE INVENTION

Achieving a balance between induction of protective immunity against pathogens and maintenance of self-tolerance is a central feature of the adaptive immune system. Although negative selection in the thymus removes the majority of clones that express T cell receptors (TCR) with high affinity for self-peptide MHC products, this process is incomplete. A significant fraction of mature peripheral T cells that respond to self-peptide—MHC complexes may differentiate into effector cells in the context of inflammatory stimuli (Bouneaud et al., 2000; Goldrath and Bevan, 1999; Slifka et al., 2003). Although this process is constrained by abortive or defective TCR signaling resulting in cellular elimination (AICD) or inactivation (Martin et al., 1999; Kearney et al., 1994), these cell-intrinsic mechanisms may not suffice to prevent the development of autoimmune disorders (Anderton et al., 2001; Panoutsakopoulou et al., 2001). There is increasing evidence that self tolerance may also depend on inhibitory interactions between effector T cells and regulatory or suppressive cells (Littman and Rudensky, 2010). However, regulatory T cells that are genetically programmed to inhibit development of autoantibody formation and autoimmune diseases have not been defined. Due to the severity and breath of autoimmune diseases such as lupus and rheumatoid arthritis, there is a great need for effective treatments of such diseases.

SUMMARY OF THE INVENTION

The invention, relates in some aspects, to the discovery of a subpopulation of CD8$^+$ regulatory T cells that are essential for maintenance of self tolerance and prevention of autoimmune disease. In some aspects, the invention involves a method for treating an autoimmune disease. The method involves administering to a subject in need of such treatment an interleukin-15 receptor (IL-15R) agonist in an amount effective to ameliorate a symptom of the autoimmune disease. In some embodiments, the autoimmune disease is selected from the group consisting of systemic lupus erythematosus, chronic graft versus host disease, rheumatoid arthritis, insulin-dependent diabetes mellitus, multiple sclerosis, psoriasis, inflammatory bowel disease, Sjogren's syndrome, Graves disease, Crohn's disease, Waldenstrom's macroglobulinemia, hyperviscosity syndrome, monoclonal gammopathy of undetermined origin, POEMS syndrome, myeloma, macroglobulinemia, and cold agglutinin disease. In some embodiments, the autoimmune disease comprises antibodies to a self antigen and the subject has the antibodies to the self antigen. In some embodiments, the IL-15R agonist is a IL-15 polypeptide that comprises a sequence at least 90% identical to the amino acid sequence of SEQ ID NO:1 and binds an IL-15R. In some embodiments, the agonist is a IL-15 polypeptide that comprises a sequence at least 95%, at least 98%, or at least 99% identical to the amino acid sequence of SEQ ID NO:1. In some embodiments, the agonist is a IL-15 polypeptide that comprises SEQ ID NO:1. In some embodiments, the agonist is an anti-IL15R antibody or an antigen-binding fragment thereof. In other embodiments, the agonist is a heterocomplex of IL-15 linked to soluble IL-15 receptor alpha chain via a GS linker.

According to one aspect of the invention, a method for treating an autoimmune disease in a subject using CD44$^+$CD122$^+$Kir$^+$ CD8$^+$ Treg cells is provided. The method comprises isolating T cells from the subject in need of such treatment, wherein the isolated T cells comprise a number of CD44$^+$CD122$^+$Kir$^+$ CD8$^+$ Treg cells; growing the isolated cells in a culture medium containing IL-15 and IL-21 in the presence of Concanavalin A activated and irradiated syngeneic CD4 T cells until the number of CD44$^+$CD122$^+$Kir$^+$ CD8$^+$ Treg cells increases by at least 5%, thereby producing a population of cells enriched with CD44$^+$CD122$^+$Kir$^+$ CD8$^+$ Treg cells; and administering CD44$^+$CD122$^+$Kir$^+$ CD8$^+$ Treg cells from the population of cells to the subject in an amount effective to ameliorate a symptom of the autoimmune disease. The CD44$^+$CD122$^+$Kir$^+$ CD8$^+$ Treg cells from the population of cells are separated from the culture medium before administration to the subject. In some embodiments, the CD8$^+$ T Cells are isolated from the subject. The CD44$^+$CD122$^+$Kir$^+$ CD8$^+$ Treg cells from the population of cells may be administered by intravenous injection. In some embodiments, the isolated cells are grown until the number of CD44$^+$CD122$^+$Kir$^+$ CD8$^+$ Treg cells increases by at least 10%, at least 20%, at least 30%, at least 50%, at least 75%, at least 90%, at least 95% or at least 100%. The population of cells enriched with CD44$^+$CD122$^+$Kir$^+$ CD8$^+$ Treg cells is further enriched by depleting a population of non-CD44$^+$CD122$^+$Kir$^+$ CD8$^+$ Treg cells. In some embodiments, a portion of CD44$^+$CD122$^+$Kir$^+$ CD8$^+$ Treg cells from the population of cells is administered to the subject. In some embodiments, all CD44$^+$CD122$^+$Kir$^+$ CD8$^+$ Treg cells from the population of cells are administered to the subject.

According to some aspects of the invention, a composition comprising CD8$^+$ cells, wherein at least 5% of the CD8$^+$ cells in the composition are CD44$^+$CD122$^+$Kir$^+$ CD8$^+$ Treg cells is provided. In some embodiments, at least 10%, at least 20%, at least 30%, at least 50%, at least 75%, at least 90%, at least 95% or 100% of the CD8$^+$ cells in the composition are CD44$^+$CD122$^+$Kir$^+$ CD8$^+$ Treg cells. The invention also involves, in some aspects, a pharmaceutical composition comprising a composition of CD8$^+$ cells, wherein at least 5% of the CD8$^+$ cells in the composition are CD44$^+$CD122$^+$Kir$^+$ CD8$^+$ Treg cells, and a pharmaceutically acceptable carrier. In some embodiments, the pharmaceutical composition further comprises an immunosuppressive agent.

According to some aspects of the invention, a method for stimulating an immune response to an antigen is provided.

The method comprises administering to a subject having the antigen and in need of immune stimulation to the antigen an agent that inhibits the proliferation and/or activity of $CD44^+$ $CD122^+Kir^+$ $CD8^+$ Treg cells in an amount effective to stimulate an immune response in the subject to the antigen. In some embodiments, the subject has an infection with a pathogen and the pathogen comprises the antigen. In some embodiments, the subject has cancer, the cancer comprises the antigen, and the antigen is a tumor antigen. The antigen may be administered to the subject in a vaccine. The agent that inhibits the proliferation and/or activity of $CD44^+$ $CD122^+Kir^+$ $CD8^+$ Treg cells can be an anti IL-15 antibody, an antibody that binds $CD44^+CD122^+Kir^+$ $CD8^+$ Treg cells, an anti-CD8 antibody, or an anti-Kir antibody. In some embodiments, the antibody is a bispecific antibody comprising a first antigen-binding domain that binds to a first surface marker present on the $CD44^+CD122^+Kir^+$ $CD8^+$ Treg cells; and a second antigen-binding domain that binds to a second surface marker present on the $CD44^+CD122^+Kir^+$ $CD8^+$ Treg cells. The first and second surface markers on the $CD44^+CD122^+Kir^+$ $CD8^+$ Treg cells may be selected from the group consisting of CD44, CD122, Kir, and CD8. In some embodiments, the agent is a composition comprising a sub-optimal dose of a first antibody that binds a first surface antigen present on $CD44^+CD122^+Kir^+$ $CD8^+$ Treg cells, and a sub-optimal dose of a second antibody that binds a second surface antigen present on the $CD44^+CD122^+Kir^+$ $CD8^+$ Treg cells, wherein the first surface antigen is different from the second surface antigen. The first antibody binds an antigen selected from the group consisting of CD44, CD122, Kir, and CD8 and the second antibody binds an antigen selected from the group consisting of CD44, CD122, Kir, and CD8.

Each of the embodiments and aspects of the invention can be practiced independently or combined. Also, the phraseology and terminology used herein is for the purpose of description and should not be regarded as limiting. The use of "including", "comprising", or "having", "containing", "involving", and variations thereof herein, is meant to encompass the items listed thereafter and equivalents thereof as well as additional items.

These and other aspects of the inventions, as well as various advantages and utilities will be apparent with reference to the Detailed Description. Each aspect of the invention can encompass various embodiments as will be understood.

All documents identified in this application are incorporated in their entirety herein by reference.

BRIEF DESCRIPTION OF THE DRAWINGS

FIG. 1 shows Qa-1 dependent suppression of Ab response by $CD44^+CD122^+$ CD8 T cells.

FIG. 2 shows that $CD44^+CD122^+Ly49^+$ CD8 T cells account for Qa-1 restricted suppressive activity. FIG. 2A: WT B6 mice were immunized i.p. with 100 µg KLH in CFA and 10 days later surface expression of CD44, CD122, Ly49 subtypes, CD8 and CD62L was analyzed. Numbers are percentage of cells expressing each surface protein.

FIG. 6 shows the amino acid sequence of human IL-15 (SEQ ID NO: 1; NCBI Reference Sequence: NP_000576.1).

FIG. 8 shows the genetic characterization of $CD44^+$ $CD122^+Ly49^+CD8^+$ Treg cells.

FIG. 9 shows the phenotypic characterization of Helios+ Ly49+ CD8+ T cells.

DETAILED DESCRIPTION OF THE INVENTION

Figure 1A:
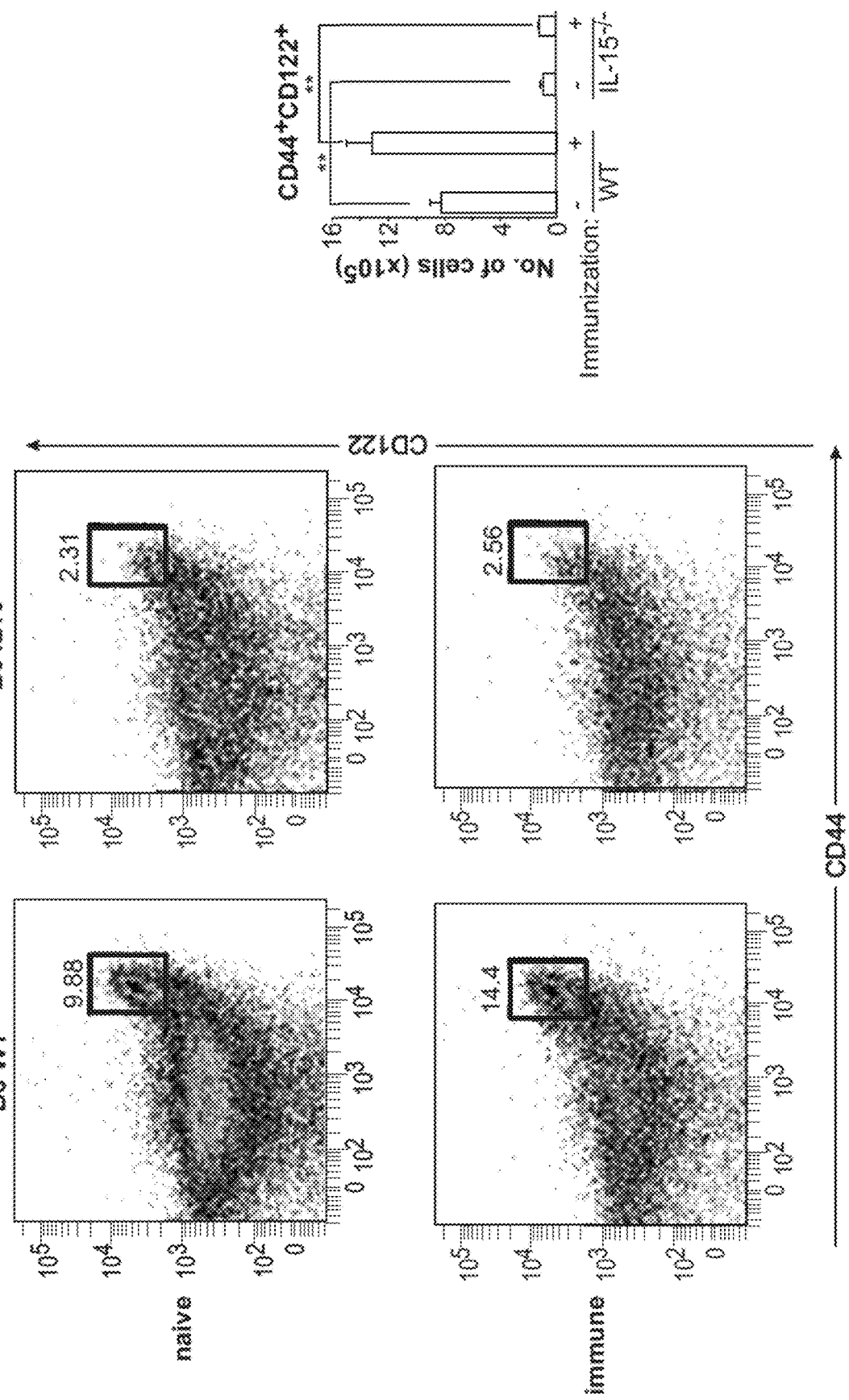
FIG. 1A shows the percentage and number of $CD44^+CD122^+CD8$ T cells from nave and KLH/CFA immunized (d 8) WT or IL-15$^{-/-}$ mice. FACS profiles are shown after gating on $CD3^+CD8^+$ cells.

The present invention, in one aspect, relates to the discovery of a subpopulation of CD8+ regulatory T cells that are essential for maintenance of self tolerance and prevention of autoimmune disease. These CD8 T cells are programmed to suppress rather than activate immunity and represent an essential regulatory element of the immune response and a guarantor of self tolerance.

The specialized regulatory CD8+ T cells selectively suppress CD4+ follicular helper T cell (TFH) activity through recognition of class I MHC peptide Qa-1 (mouse homolog of human leukocyte antigen E (HLA-E)) expressed at the surface of TFH cells and dampen autoantibody responses. An analysis of the surface phenotype of these CD8+ regulatory (Treg) cells indicated that they expressed high levels of CD44 and CD122, relatively lower levels of CXCR5 and ICOSL, and also express the Kir receptor (immunoglobulin like killer inhibitory receptor; designated Ly49 in mice). DNA microarray with cDNA prepared from mouse Ly49+ and Ly49− CD8+ T cells also identified the transcription factor Helios as a potential master transcription factor for genes that are important for the CD8 Treg development and function.

Helios is a member of the Ikaros family of zinc finger regulators. Helios is highly expressed at early stages of T cell development and also expressed in a subset (~70%) of FoxP3+CD4+ Treg cells; however, Helios expression is not dependent on FoxP3 expression. Mature B cells, dendritic cells and myeloid cells do not express Helios. Helios expression and function in the CD8 T cell pool has not been reported. The inventors have shown that Helios is exclusively expressed by Ly49+ CD8 Treg within the CD8 T cell pool and expression of this transcription factor in Ly49+ T cells is associated with their suppressive function. The presence of Helios protein and mRNA can detected by intracellular staining of Helios using antibodies and quantitative PCR (Expression of Helios, an Ikaros Transcription Factor Family Member, Differentiates Thymic-Derived from Peripherally Induced Foxp3+ T Regulatory Cells; Thornton et al. J Immunol 2010 184:3433-3441). Helios expression in cells can be detected, for example, by testing an aliquot of the cells for the presence of Helios protein or mRNA. Expression of Helios protein can be detected by staining spleen cells from mice (or PBMC from humans) with surface markers, for example CD3, CD8, CD44, CD122 and Ly49 (KIR in humans). Cells are then fixed with fixation buffer (4% paraformaldehyde in phosphate-buffered saline) and washed with permeabilization buffer (0.1% saponin and 0.009% sodium azide in phosphate-buffered saline). Subsequent staining with anti-Helios antibody in permeabilization buffer allows detection of the expression (as a %) of Helios in this subset of CD8$^+$ T cells and allows definition of additional surface markers expressed by Helios$^+$CD8 cells in mouse and man.

Expression of CD122 on their surface is in accord with their dependence on IL-15 for both development and function. Expression of the class I MHC receptor Ly49 by CD8 cells has also been associated with enhanced responsiveness to IL-15 (Coles et al., 2000; Judge et al., 2002; Anfossi et al., 2004). The CD44$^+$CD122$^+$Kir$^+$Helios$^+$ CD8$^+$ T cells, which represent 3-5% of CD8 T cells, account for virtually all of the Qa-1-restricted suppressive activity in this T cell subset.

The specialized regulatory CD8$^+$ T cells are used according to the invention to treat autoimmune diseases. As used here, the specialized regulatory CD8$^+$ T cells include CD44$^+$CD122$^+$Helios$^+$ CD8$^+$ Treg cells, CD44$^+$CD122$^+$Helios$^+$Kir$^+$CD8$^+$ Treg cells, and/or CD44$^+$CD122$^+$Kir$^+$ CD8$^+$ Treg cells.

Aspects of the invention involve methods of treating autoimmune diseases by isolating T cells from the subject in need of such treatment, growing the cells in a culture medium enriched with IL-15 and IL-21 in the presence of Concanavalin A activated and irradiated syngeneic CD4 T cells such that the population of CD44$^+$CD122$^+$Helios$^+$ CD8$^+$ Treg cells increases in number by at least 5%, thereby producing a population of cells enriched with CD44$^+$CD122$^+$Helios$^+$ CD8$^+$ Treg cells. Then CD44$^+$CD122$^+$Helios$^+$ CD8$^+$ Treg cells from the population are administered to the subject in an amount effective to ameliorate a symptom of the autoimmune disease. In some embodiments, CD44$^+$CD122$^+$Helios$^+$ CD8$^+$ Treg also express Kir, and CD44$^+$CD122$^+$Helios$^+$ Kir$^+$CD8$^+$ Treg from the population can be administered to human subjects in an amount sufficient to ameliorate symptoms of autoimmune disease.

In some embodiments, the T cells isolated from the subject are enriched for CD8$^+$ cells prior to growing the isolated cells in the culture medium. In some embodiments, CD8$^+$ T cells are isolated prior to growing them in the culture medium. As used herein, the term "isolated" refers to removal of a sample comprising T cells from the subject and further separating the T cells from other non-T cells. In some embodiments, the cells are grown in RPMI medium supplemented with 10% FCS, β-mercaptoethanol, 1M Sodium Pyruvate, 10 mM Hepes Buffer, 2 mM L-Glutamine, 50 Units/ml Penicillin and 50 μg/ml Streptomycin. In some embodiments, the isolated cells are grown until the population of the specialized regulatory CD8$^+$ T cells in the isolated cells increases in number by at least 5%, 10%, at least 20%, at least 30%, at least 50%, at least 75%, at least 90%, at least 100%, or at least 200%. In some embodiments, after the isolated T cells are grown, the specialized regulatory CD8$^+$ T cells are further enriched by depleting one or more cell types other than the CD44$^+$CD122$^+$Helios$^+$ CD8$^+$ Treg cells, the CD44$^+$CD122$^+$Helios$^+$Kir$^+$ CD8$^+$ Treg cells and the CD44$^+$CD122$^+$Kir$^+$ CD8$^+$ Treg cells. In some embodiments, the specialized regulatory CD8$^+$ T cells are administered to the subject by intravenous injection. The specialized regulatory CD8$^+$ T cells are separated from the culture medium before administration to the subject. The specialized regulatory CD8$^+$ T cells are administered to the subject in an amount effective to ameliorate a symptom of the autoimmune disease.

In some embodiments, the specialized regulatory CD8$^+$ T cells are administered in combination with an autoimmune drug. Non-limiting examples of such drugs include methotrexate, cyclophosphamide, Imuran (azathioprine), cyclosporin, and steroid compounds such as prednisone and methylprednisolone.

The specialized regulatory CD8$^+$ T cells depend on IL-15 for activation of suppressive activity. Accordingly, aspects of the invention involve methods of treating autoimmune diseases by enhancing the activity of the specialized regulatory CD8$^+$ T cells using an interleukin-15 receptor (IL-15R) agonist in an amount effective to ameliorate a symptom of the autoimmune disease.

In some embodiments, a subject in need of treatment of autoimmune disease is a subject identified as having an autoimmune disease, i.e. the subject has been diagnosed by a physician (e.g., using methods well known in the art) as having an autoimmune disease. In some embodiments, the subject in need of treatment is a subject suspected of having or developing an autoimmune disease, such as a subject presenting one or more symptoms indicative of an autoimmune disease. In some embodiments, a subject suspected of having an autoimmune disease may display abnormal titers of autoantibodies. The subject having abnormal titers of autoantibodies may have at least one other symptom of autoimmune disease or may be without other symptoms associated with autoimmune disease. The term "subject in need of treatment" further includes people who once had an autoimmune disease but whose symptoms have ameliorated.

The subject is an animal, typically a mammal. In one aspect, the subject is a dog, a cat, a horse, a sheep, a goat, a cow or a rodent. In important embodiments, the subject is a human. It is understood that humans and mice share similar T cell markers in many instances designated similarly. For example, human and mice both have CD44, CD122 and CD8. In case of one marker important to the subject matter of the invention, the designation is different. The marker Ly49 in mice is designated Kir (immunoglobulin-like killer inhibitory receptors) in humans. To the extent that the claims and description refer to the treatment of humans and markers and antibodies are discussed, it is intended that the marker is human and the antibody binds the human marker.

As used herein, a compound is an IL-15R agonist when, like IL-15, it binds IL-15R and induces proliferation/activation of the specialized regulatory CD8$^+$ T cells. In some embodiments, the agonist induces a biological response that is of a similar or higher level than the one induced by native IL-15. Some agonists induce an even higher level of biological response (super-agonist). An IL-15R agonist typically has an affinity for binding to IL-15 receptor alpha and/or to IL-15 receptor beta/gamma that is similar to that of native IL-15. Examples of such agonists include, but are not limited to: IL-15 polypeptide having the amino acid sequence of SEQ ID NO:1 (IL-15) and polypeptides that comprises a sequence at least 90%, at least 95%, at least 98% or at least 99% identical to the amino acid sequence of SEQ ID NO:1 (IL-15); agonistic anti-IL-15R antibody, or an antigen-binding fragment thereof; heterocomplex of IL-15 linked to soluble IL-15 receptor alpha chain (sushi domain) via a GS linker (recombinant IL-15/IL-15RA complex) (see e.g., U.S. application Ser. No. 12/090,930 the entire contents of which are incorporated by reference). In any of the embodiments, the IL-15R may be human IL-15R and the IL-15R receptor agonist is an agonist of human IL-15R.

The amino acid sequence of human IL-15 is represented by NCBI Reference Sequence: NP_000576.1 (SEQ ID NO:1). IL-15 polypeptides also include fragments of IL-15, such as amino acids 49-162 of SEQ ID NO:1, which has previously been characterized as a mature form of IL-15 derived by proteolytic cleavage of a leader sequence from the polypeptide of SEQ ID NO:1, and other fragments that retain the biological activity of IL-15 are encompassed by the term IL-15. IL-15 analogs, including derivative or variants of IL-15 having one or more substituted amino acid, that exhibit the biological activity of IL-15 are also included within the meaning of the term IL-15R agonist. Exemplary analogs are described in U.S. application Ser. No. 11/639,877, U.S. Pat. No. 5,552,303, and in Bernard et al, J. Biol. Chem. 279:24313-24322, 2004, which are incorporated herein by reference. The term, IL-15 also encompasses IL-15 of species other than human, such as nonhuman primates, mouse, rat, pig, horse, cow, dog, etc.

A self antigen (or auto-antigen) is a subject's self-produced constituent, against which the subject mounts an undesired immune response. An "autoantibody" is an antibody produced by a subject, which binds to one or more of the subject's own constituents or self antigens. The term 'autoimmune disease' refers to those disease states and conditions wherein the immune response of the patient is directed against the patient's own constituents resulting in an undesirable and often terribly debilitating condition. As used herein, 'autoimmune disease' is intended to further include autoimmune conditions, syndromes and the like. Example of autoimmune diseases include, but are not limited to systemic lupus erythematosus, chronic graft versus host disease, rheumatoid arthritis, insulin-dependent diabetes mellitus, multiple sclerosis, psoriasis, inflammatory bowel disease, Sjogren's syndrome, Graves disease, Crohn's disease, Waldenstrom's macroglobulinemia, hyperviscosity syndrome, monoclonal gammopathy of undetermined origin, POEMS syndrome, myeloma, macroglobulinemia, and cold agglutinin disease. In some embodiments, the autoimmune disease involves antibodies to a self antigen and the subject has the antibodies to the self antigen.

The specialized regulatory $CD8^+$ T cells or the IL-15R agonist are administered in an effective amount. An effective amount is a dose sufficient to provide a medically desirable result and can be determined by one of skill in the art using routine methods. In some embodiments, an effective amount is an amount which results in any improvement in the condition being treated. In some embodiments, an effective amount may depend on the type and extent of the autoimmune disease or condition being treated and/or use of one or more additional therapeutic agents. However, one of skill in the art can determine appropriate doses and ranges of therapeutic agents to use, for example based on in vitro and/or in vivo testing and/or other knowledge of compound dosages.

When administered to a subject, effective amounts of the therapeutic agent will depend, of course, on the particular disease being treated; the severity of the disease; individual patient parameters including age, physical condition, size and weight, concurrent treatment, frequency of treatment, and the mode of administration. These factors are well known to those of ordinary skill in the art and can be addressed with no more than routine experimentation. In some embodiments, a maximum dose is used, that is, the highest safe dose according to sound medical judgment.

In the treatment of autoimmune disease, an effective amount is that amount which slows the progression of the disease, halts the progression of the disease, or reverses the progression of the disease. An effective amount includes that amount necessary to slow, reduce, inhibit, ameliorate or reverse one or more symptoms associated with the autoimmune disease. In some embodiments, such terms refer to a reduction in the swelling of one or more joints or a reduction in the pain, fatigue and/or fever associated with an autoimmune disorder. In some embodiments, such terms refer to a reduction in the levels of circulating autoantibodies associated with the autoimmune disease. In some embodiments, such terms refer to a reduction in a human's PASI score. In some embodiments, such terms refer to an improvement in a human's global assessment score.

An effective amount of a compound typically will vary from about 0.001 mg/kg to about 1000 mg/kg in one or more dose administrations, for one or several days (depending of course of the mode of administration and the factors discussed above).

Actual dosage levels of the therapeutic agent can be varied to obtain an amount that is effective to achieve the desired therapeutic response for a particular patient, compositions, and mode of administration. The selected dosage level depends upon the activity of the particular compound, the route of administration, the tissue being treated, and prior medical history of the patient being treated. However, it is within the skill of the art to start doses of the compound at levels lower than required to achieve the desired therapeutic effort and to gradually increase the dosage until the desired effect is achieved.

According to some aspects of the invention, a composition is provided. The composition comprises $CD44^+CD122^+Kir^+ CD8^+$ Treg cells wherein at least 5% of the $CD8^+$ cells in the composition are $CD44^+CD122^+Kir^+ CD8^+$ Treg cells. In some embodiments, at least 10%, at least 20%, at least 30%, at least 50%, at least 75%, at least 90%, at least 95% or 100% of the $CD8^+$ cells in the composition are $CD44^+CD122^+Kir^+ CD8^+$ Treg cells. According to some aspects of the invention, a pharmaceutical composition comprising a composition of $CD8^+$ cells, wherein at least 5% of the $CD8^+$ cells in the composition are $CD44^+CD122^+Kir^+ CD8^+$ Treg cells, and a pharmaceutically acceptable carrier is provided. In some embodiments, the pharmaceutical composition comprises an immunosuppressive agent. Examples of immunosuppressive agents include, but are not limited to, non-steroidal anti-inflammatory agents, cyclosporine A, FK506, anti-CD4 antibody and rapamycin.

Some aspects of the invention involve a method for stimulating an immune response to an antigen. The method comprises administering to a subject having the antigen and in need of immune stimulation to the antigen an agent that inhibits the proliferation and/or activity of $CD44^+CD122^+Kir^+ CD8^+$ Treg cells in an amount effective to stimulate an immune response in the subject to the antigen.

In some embodiments, the subject has an infection with a pathogen and the pathogen comprises the antigen. As used herein, "infection" refers to invasion of the body of a subject with an organism that has the potential to cause disease. Such organisms include, but are not limited to, viruses, bacteria, fungi and parasites.

Examples of viruses include, but are not limited to, Human immunodeficiency viruses (HIV-1 and HIV-2), Human T lymphotrophic virus type I (HTLV-I), Human T lymphotrophic virus type II (HTLV-II), Herpes simplex virus type I (HSV-1), Herpes simplex virus type 2 (HSV-2), Human papilloma virus (multiple types), Hepatitis A virus, Hepatitis B virus, Hepatitis C and D viruses, Epstein-Barr virus (EBV), Cytomegalovirus and Molluscum contagiosum virus.

Examples of bacteria include, but are not limited to, *Pasteurella* species, Staphylococci species, *Streptococcus* species, *Escherichia coli, Pseudomonas species*, and *Salmonella* species. Specific examples of infectious bacteria include but are not limited to, *Helicobacter pyloris, Borelia*

*burgdorferi, Legionella pneumophilia, Mycobacteria* sps (e.g. *M. tuberculosis, M. avium, M. intracellular, M. kansaii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (*viridans* group), *Streptococcus faecalis, Streptococcus bovis, Streptococcus* {anaerobic sps.), *Streptococcus pneumoniae*, pathogenic *Campylobacter* sp., *Enterococcus* sp., *Haemophilus influenzae, Bacillus antracis, Corynebacterium diphtheriae, corynebacterium* sp., *Erysipelothrix rhusiopathiae, Clostridium perfringers, Clostridium tetani, Enterobacter aerogenes, Klebsiella pneumoniae, Pasteurella multocida, Bacteroides* sp., *Fusobacterium nucleatum, Streptobacillus moniliformis, Treponema palladium, Treponema pertenue, Leptospira, Rickettsia*, and *Actinomyces israelii*.

Examples of fungi, but are not limited to, include *Cryptococcus neoformans, Histoplasma capsulatum, Coccidioides immitis, Blastomyces dermatitidis, Chlamydia trachomatis, Candida albicans*. Other infectious organisms (i.e., protists) include *Plasmodium* spp. such as *Plasmodium falciparum, Plasmodium malariae, Plasmodium ovale*, and *Plasmodium vivax* and *Toxoplasma gondii*. Blood-borne and/or tissues parasites include *Plasmodium* spp., *Babesia microti, Babesia divergens, Leishmania tropica, Leishmania* spp., *Leishmania braziliensis, Leishmania donovani, Trypanosoma gambiense* and *Trypanosoma rhodesiense* (African sleeping sickness), *Trypanosoma cruzi* (Chagas' disease), and *Toxoplasma gondii*.

Examples of parasites include, but are not limited to, *Plasmodium* spp., *Babesia microti, Babesia divergens, Leishmania tropica, Leishmania* spp., *Leishmania braziliensis, Leishmania donovani, Trypanosoma gambiense* and *Trypanosoma rhodesiense* (African sleeping sickness), *Trypanosoma cruzi* (Chagas' disease), and *Toxoplasma gondii*.

In some embodiments, the subject has cancer, the cancer comprises the antigen, and the antigen is a tumor antigen. The cancer can be any cancer. Cancers include, but are not limited to, biliary tract cancer; bone cancer; brain and CNS cancer; breast cancer; cervical cancer; choriocarcinoma; colon cancer; connective tissue cancer; endometrial cancer; esophageal cancer; eye cancer; gastric cancer; Hodgkin's lymphoma; intraepithelial neoplasms; larynx cancer; lymphomas; liver cancer; lung cancer; melanoma; neuroblastomas; oral cavity cancer; ovarian cancer; pancreas cancer; prostate cancer; rectal cancer; sarcomas; skin cancer; testicular cancer; thyroid cancer; and renal cancer.

The tumor antigen can be any tumor antigen. For example, the tumor antigen can be, but is not limited to human epithelial cell mucin (Muc-1; a 20 amino acid core repeat for Muc-1 glycoprotein, present on breast cancer cells and pancreatic cancer cells), the Ha-ras oncogene product, p53, carcino-embryonic antigen (CEA), the raf oncogene product, GD2, GD3, GM2, TF, sTn, MAGE-1, MAGE-3, tyrosinase, gp75, Melan-A/Mart1, gp100, HER2/neu, EBV-LMP 1 & 2, HPV-F4, 6, 7, prostatic serum antigen (PSA), Prostate Specific Membrane Antigen (PSMA), alpha-fetoprotein (AFP), C017-1A, GA733, gp72, p53, the ras oncogene product, HPV E7 and melanoma gangliosides. In some embodiments, the antigen is administered to the subject in a vaccine. This administration may supplement the presence of the antigen in the subject due to an infection or the existence of a tumor. The vaccine may also involve the introduction into the subject of the antigen for the first time. As used herein, "vaccine" means an organism or material that contains an antigen in an innocuous form. The vaccine may be recombinant or non-recombinant. Vaccines may take the form, for example, of a toxoid, which is defined as a toxin that has been detoxified but that still retains its major immunogenic determinants; or a killed organism, such as typhoid, cholera and poliomyelitis; or attenuated organisms that are the live but non-virulent, forms of pathogens, or it may be antigen encoded by such organism, or it may be a killed tumor cell or an antigen present on a tumor cell.

Antigens include but are not limited to cells, cell extracts, proteins, polypeptides, peptides, polysaccharides, polysaccharide conjugates, peptide and non-peptide mimics of polysaccharides and other molecules, small molecules, lipids, glycolipids, carbohydrates, viruses and viral extracts and multicellular organisms such as parasites and allergens (see e.g., U.S. Pat. No. 7,576,066).

An agent that inhibits the proliferation and/or activity of specialized regulatory $CD8^+$ T cells includes, but is not limited to, anti IL-15 antibody or an antibody that binds the specialized regulatory $CD8^+$ T cells. The agent can be an anti-CD8 antibody or an antibody to Kir. In some embodiments, the antibody that binds $CD44^+CD122^+Kir^+$ $CD8^+$ Treg cells is a bispecific antibody comprising a first antigen-binding domain that binds to a first surface marker present on the $CD44^+CD122^+Kir^+$ $CD8^+$ Treg cells and a second antigen-binding domain that binds to a second surface marker present on the $CD44^+CD122^+Kir^+$ $CD8^+$ Treg cells. The first and second surface markers on the $CD44^+CD122^+$ $Kir^+$ $CD8^+$ Treg cells include, but are not limited to, CD44, CD122, Kir, and CD8. In some embodiments, the agent is a composition comprising a sub-optimal dose of a first antibody that binds a first surface antigen present on $CD44^+$ $CD122^+Kir^+$ $CD8^+$ Treg cells, and a sub-optimal dose of a second antibody that binds a second surface antigen present on the $CD44^+CD122^+Kir^+$ $CD8^+$ Treg cells, wherein the first surface antigen is different from the second surface antigen. The first antibody binds an antigen selected from the group consisting of CD44, CD122, Kir and CD8 and the second antibody binds an antigen selected from the group consisting of CD44, CD122, Kir, and CD8.

In some embodiments, the agent that inhibits the proliferation and/or activity of specialized regulatory $CD8^+$ T cells is an agent that decreases the expression levels and/or activity of Helios in the cells. The agent that inhibits Helios levels and/or activity can be one or more of: a Helios binding protein that binds and inhibits Helios activity, e.g., DNA binding activity, nuclear translocation activity, homo or heterodimerization activity, or transcriptional activation activity; an antibody that specifically binds to the Helios protein, e.g., an antibody that disrupts Helios' ability to bind DNA or another transcription factor, to translocate to the nucleus, or bind DNA; a mutated inactive Helios or fragment thereof which, e.g., binds to Helios binding partner (e.g., DNA or another transcription factor, e.g., Ikaros or Aiolos factor) but disrupts Helios activity, e.g., nuclear translocation activity or transcriptional activation activity; a Helios nucleic acid molecule that can bind to a cellular Helios nucleic acid sequence, e.g., mRNA, and inhibit expression of the protein, e.g., an antisense molecule, siRNA; an agent which decreases Helios gene expression, e.g., a small molecule which binds the promoter of Helios and decreases Helios gene expression.

In some embodiments, the agent is a an agent that recognizes one of the markers present on the specialized regulatory $CD8^+$ T cells coupled to a toxin. The agent that recognizes one of the markers present on the $CD44^+CD122^+$ $Kir^+$ $CD8^+$ Treg cells could be a ligand specific to one of the markers, or an antibody to one of the markers. Examples of toxins include, but are not limited to biological toxins, chemical toxins, synthetic toxins and radionuclides. The radionuclides can be selected from the group consisting of beta emitting metallic radionuclides, alpha emitters and gamma emitters. Examples of radionuclides include, but are not limited to, $^{123}$I, $^{125}$I, $^{130}$I, $^{131}$I, $^{133}$I, $^{135}$I, $^{128}$Ba, $^{13}$N, $^{15}$O, and $^{18}$F.

As used herein, a sub-optimal amount of an antibody is an amount that if used alone would not be an effective and/or optimal amount to inhibit the activity of the specialized regulatory CD8$^+$ T cells to treat the condition, but when used in combination with the second antibody would be an effective and/or optimal amount to inhibit the activity of the specialized regulatory CD8$^+$ T cells to treat the condition. The use of sub-optimal doses of therapeutic agents is useful because it allows for a reduction in any potential side effects of the antibodies.

The agent that inhibits the proliferation and/or activity of the specialized regulatory CD8$^+$ T cells is administered in an amount effective to stimulate an immune response to the antigen in the subject. The term "effective amount" as provided herein, refers to a sufficient amount of the agent to provide an immunological response and corresponding therapeutic effect. The exact amount required will vary from subject to subject, depending on the species, age, and general condition of the subject, the severity of the condition being treated, and the particular agent, mode of administration, and the like. An appropriate "effective" amount in any individual case may be determined by one of ordinary skill in the art using routine experimentation.

Pharmaceutical preparations and compounds are administered to a subject by any suitable route. For example, compositions can be administered orally, including sublingually, rectally, parenterally, intracisternally, intravaginally, intraperitoneally, topically and transdermally (as by powders, ointments, or drops), bucally, or nasally. The pharmaceutical preparations of the present invention may include or be diluted into a pharmaceutically-acceptable carrier. The term "pharmaceutically-acceptable carrier" as used herein means one or more compatible fillers, diluants or other such substances, which are suitable for administration to a human or other mammal such as a dog, cat, or horse. The term "carrier" denotes an organic or inorganic ingredient, natural or synthetic, with which the active ingredient is combined to facilitate the application. The carriers are capable of being commingled with the preparations of the present invention, and with each other, in a manner such that there is no interaction which would substantially impair the desired pharmaceutical efficacy or stability. Carriers suitable for oral, subcutaneous, intravenous, intramuscular, etc. formulations can be found in Remington's Pharmaceutical Sciences, Mack Publishing Company, Easton, Pa.

The present invention is further illustrated by the following Example, which in no way should be construed as further limiting. The entire contents of all of the references (including literature references, issued patents, published patent applications, and co-pending patent applications) cited throughout this application are hereby expressly incorporated by reference.

EXAMPLE

Materials and Methods
Mice.

C57BL/6J (B6), Rag2$^{-/-}$, IL-15$^{-/-}$ and B6.Qa-1(D227K) mice (backcrossed for 11 generations) were housed in pathogen-free conditions. All experiments were performed in compliance with federal laws and institutional guidelines as approved by Dana Farber Cancer Institute's Animal Care and Use Committee.

Reagents and Flow Cytometry.

Single-cell suspensions were prepared and maintained in the dark at 4° C. for immunofluorescent analysis, washed in ice-cold FACS buffer (2% fetal calf serum, 0.1% NaN3 in PBS) and incubated with each antibody for 30 min and washed with FACS buffer before analyzing. Anti-CD4, anti-CD8, anti-B220, anti-CD44, anti-CD62L, anti-Fas, anti-ICOS, anti-IgM, anti-CD200 (BD Bioscience) or anti-CD8β, anti-Ly49C/I/F/H, anti-Ly49A, Ly-49G2, Ly49C/I, Ly49D, Ly49F, Ly49H (eBioscience) were used followed by analysis of cells using a FACSCanto (BD Biosciences) and FlowJo software (TriStar).

Cell Purification and Adoptive Transfer.

Naïve B cells were isolated from spleen of Qa-1 WT and mutant mice (BD Bioscience). Naïve CD4$^+$CD25$^-$ cells were purified from spleens of Qa-1 WT and mutant mice using a CD4 cell enrichment kit (BD Bioscience) and biotinylated anti-CD25 Ab. B cell and CD4 cell purity was >95%. To generate immune CD8 cells, WT B6 mice were immunized i.p. with 100 μg KLH in CFA and splenic CD8 cells obtained 7-10 days later (BD Bioscience) and sorted for CD44$^+$CD122$^+$Ly49$^+$ CD8 T cells. These cells were transferred into Rag2$^{-/-}$ recipients intravenously. Immediately after cell transfer, Rag2$^{-/-}$ mice were immunized i.p. with 100 μg NP$_{19}$-KLH in CFA and reimmunization i.p. with 50 μg NP$_{19}$-KLH in IFA. ELISA. For detection of NP specific antibodies, ELISA plates were coated with 0.5 μg/ml NP$_4$-BSA or 1 μg/ml NP$_{23}$-BSA (Biosearch Technologies) and serum harvested 14 days after immunization with NP$_{19}$-KLH in CFA and reimmunization with NP$_{19}$-KLH in IFA was used as a standard. 1:4000 dilution of this immune serum was defined as 100 units/ml. Total IgG, IgG1 and IgG2a were detected by incubating plates with biotinylated anti-mouse IgG, IgG1 or IgG2a followed by streptavidin-peroxidase. For the detection of autoantibodies, porcine thyroglobulin (Sigma) and porcine insulin (Sigma) were used to detect relevant Ab.

Statistics.

Statistical analyses were performed using Wilcoxon-Mann-Whitney rank sum test for comparison of two conditions and Kruskal-Wallis test for comparison of more than two conditions. P value<0.05 was considered statistically significant (*=<0.05, =<0.01, *=<0.001).

Results

CD8$^+$ Treg Depend on IL-15 for Acquisition of Suppressive Activity

CD44$^+$ CD8$^+$ cells are composed of a CD122$^+$ IL-15-dependent fraction and a CD122$^-$ IL-15-independent fraction (FIG. 1A). Analysis of CD8$^+$CD44$^+$CD122$^+$ cells from WT and IL-15$^{-/-}$ mice showed that WT mice displayed 5-fold more CD8$^+$CD44$^+$CD122$^+$ cells compared to IL-15$^{-/-}$ mice. Immunization of WT mice with KLH in CFA induced a ~50% increase of CD44$^+$CD122$^+$ CD8 T cells but no detectable increase in IL-15$^{-/-}$ mice (FIG. 1). Further analysis of the residual population of CD44$^+$CD122$^+$ CD8 cells from IL-15$^{-/-}$ mice showed that these cells expressed considerably lower levels of CD122 (FIG. 1A, left panel).

These data suggest that defective suppressive activity of CD44$^+$CD8$^+$ T cells from IL-15$^{-/-}$ donors might reflect a failure to generate CD122$^+$CD44$^+$ CD8 T cells. To test Qa-1-dependent suppressive activity of CD44$^+$CD122$^+$CD8 cells, we sorted CD44$^+$CD122$^+$CD8$^+$ cells (>98% purity) or CD44$^+$CD122$^-$ CD8$^+$ cells (>96% purity) from WT B6 mice and transferred them into Rag2$^{-/-}$ hosts along with (CD25$^-$)

Figure 1B:
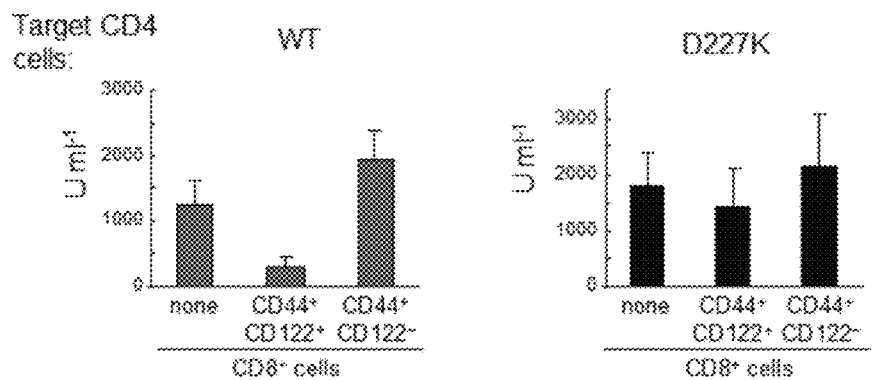
FIG. 1B shows Ab response after transfer of B, CD4 and CD8 cells into Rag2$^{-/-}$ mice. $2\times10^6$ WT nave B cells were transferred along with $1\times10^6$ CD25$^+$ depleted CD4 cells from B6.Qa-1(WT) or B6.Qa-1(D227K) mice into Rag2$^{-/-}$ hosts. $CD44^+$ $CD122^+$ or $CD44^+CD122^-$ CD8$^+$ T cells isolated from KLH/CFA immunized WT B6 mice were also transferred into these Rag2$^{-/-}$ hosts before recipients were immunized i.p. with 100 µg NP19-KLH in CFA. At day 10, mice were challenged i.p. with 50 µg NP19-KLH in IFA and NP specific Ab responses were measured by ELISA seven days later.

CD4 cells from Qa-1 (WT) or Qa-1 (D227K) donors and B cells. After challenge with $NP_{19}$-KLH, recipients of $CD44^+CD122^+$ CD8 cells, but not $CD44^+CD122^-$ cells, displayed Qa-1-restricted suppression of NP-specific Ab responses (FIG. 1B). In contrast, the $CD44^+CD122^-$ CD8 cells did not suppress.

Figure 1C:
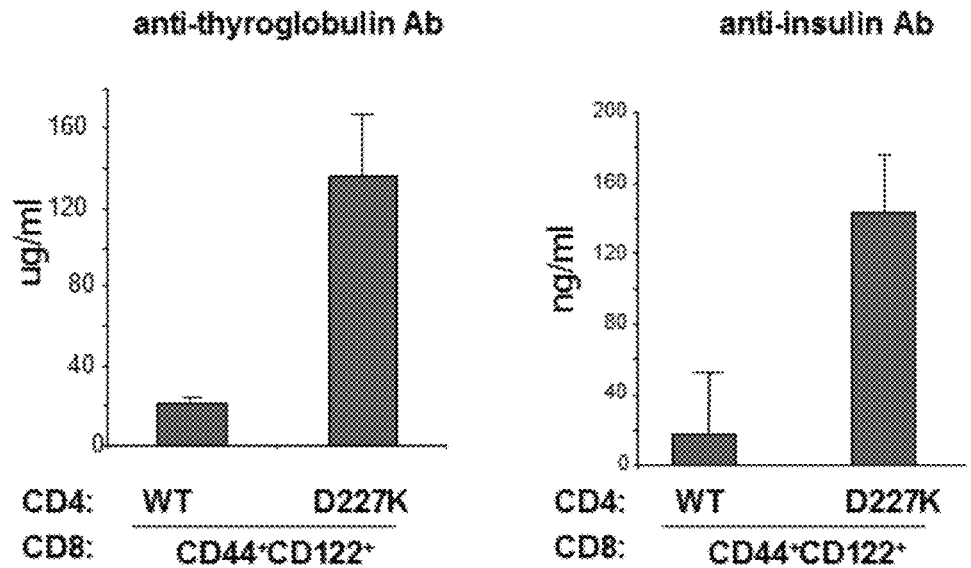
FIG. 1C shows defective inhibition by CD8 Treg leads to autoantibody generation. Anti-thyroglobulin and anti-insulin Ab generated in Rag2 recipients were measured by ELISA at day 50.

The generation of a high affinity Ab response is a precisely orchestrated process that depends on the activation of germinal center (GC) B cells by $T_{FH}$ cells. The D227K mutation of Qa-1 disrupts the inhibitory interaction between $CD8^+$ Treg and $Qa-1^+$ target $T_H$ cells. This defective inhibitory interaction allows robust autoantibody responses to thyroglobulin and insulin, even in the presence of high numbers of $CD8^+$ Treg (FIG. 1C).

Expression of Ly49 by $CD8^+$ Treg.

$CD44^+CD122^+CD8$ T cells are divisible into two subsets according to expression of Ly49. The $Ly49^+$ CD8 cells are particularly responsive to activation by IL-15 in vitro and depend on $CD4^+$ T cells for efficient development and age-dependent expansion in vivo (Coles et al., 2000; Anfossi et al., 2004).

Immunization of WT B6 mice with KLH/CFA doubled the numbers of $CD44^+CD122^+$ CD8 T cells and 25% of these cells also express Ly49. These $CD44^+CD122^+Ly49^+$ cells also express $CD8\alpha\beta^+$ and not $CD8\alpha\alpha$ as well as high levels of CD62L (FIG. 2a). Additional analysis revealed that the $Ly49^+$ CD8 subset expressed the following inhibitory receptors: Ly49A (24.8%), Ly49C/I (13.1%), Ly49F (90%) and Ly49G2 (33%); activating Ly49 receptors (Ly49D,H) were not expressed at detectable levels by these cells (FIG. 2a).

Figure 2B:
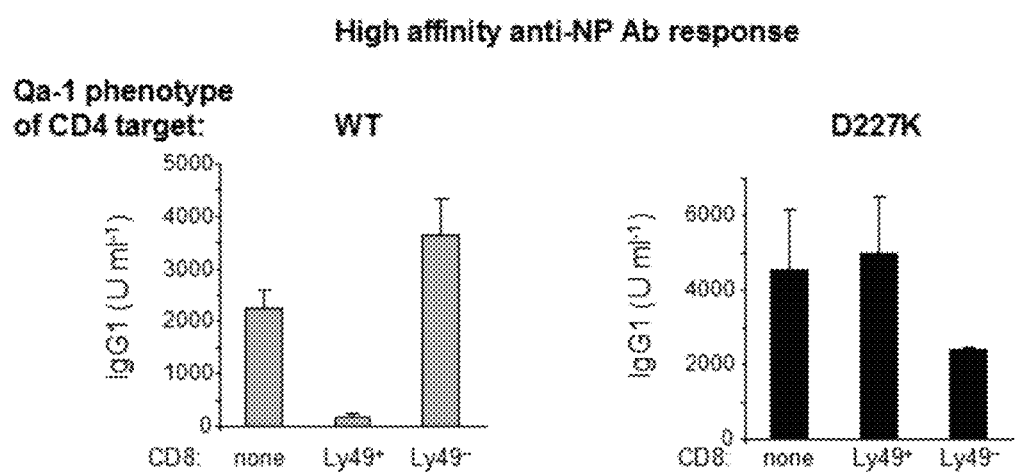
FIG. 2B shows the Ab response after transfer of B, CD4 and CD8 cells into Rag2$^{-/-}$ hosts. $2\times10^6$ WT nave B cells were transferred along with $0.5\times10^6$ CD25$^+$ depleted CD4 cells from B6.Qa-1(WT) or B6.Qa-1(D227K) mice into Rag2$^{-/-}$ hosts. $CD44^+CD122^+Ly49^+$ CD8$^+$ T cells were isolated from KLH/CFA immunized WT B6 mice and $0.15\times10^6$ cells were transferred into Rag2 hosts. Immediately after cell transfer, Rag2$^{-/-}$ recipients were immunized i.p. with 100 µg NP19-KLH in CFA. At day 10, mice were challenged i.p. with 50 µg NP19-KLH in IFA and high affinity NP specific Ab responses were measured by ELISA seven days after challenge.

Sorted $CD44^+CD122^+Ly49^+$, but not $CD44^+CD122^+Ly49^-$, CD8 T cells efficiently suppressed Qa-1 WT CD4 T cells, but not Qa-1 mutant (D227K) CD4 T cells, i.e. suppressive activity depended on recognition of Qa-1 on target CD4 cells (FIG. 2b). These findings indicate that Ly49 expression can distinguish $CD8^+$ Treg from conventional $CD8^+$ T memory cells and open the possibility that development of $CD8^+$ Treg may depend in part on engagement of Ly49 by class I MHC.

Figure 3:
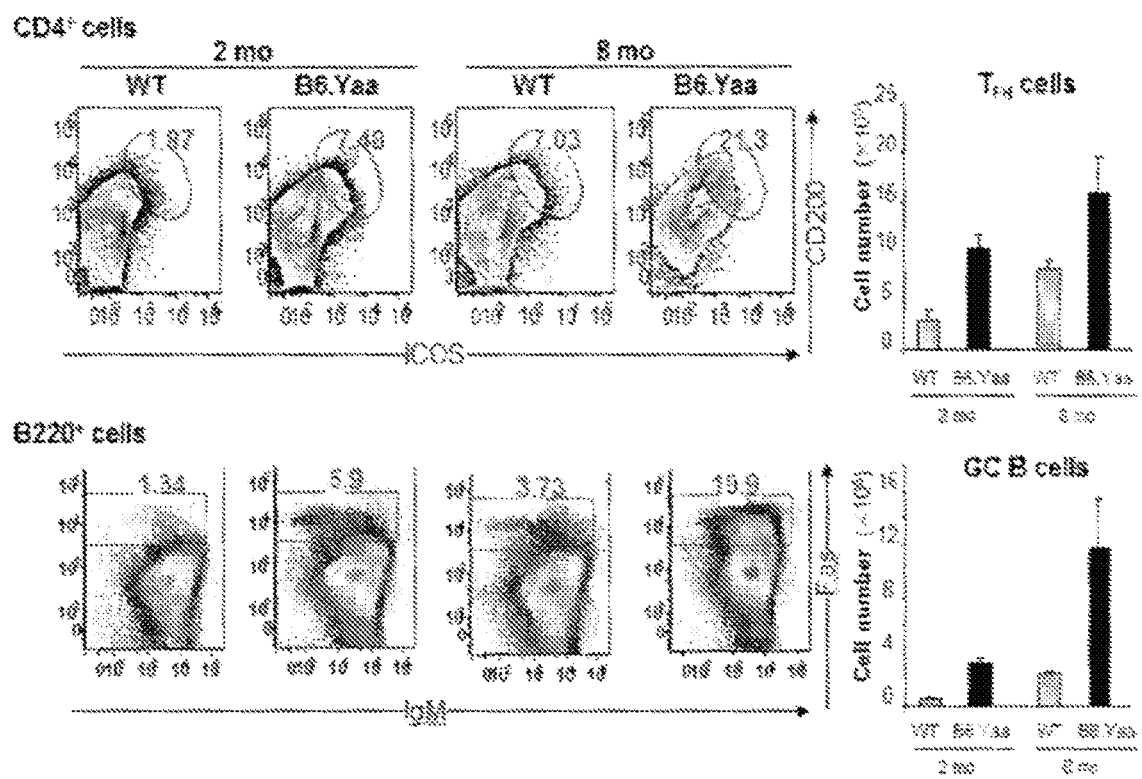
FIG. 3 shows the expansion of TFH and GC B cells in B6-Yaa mice. Spleen cells from age matched (2 mo and 8 mo) WT B6 and B6-Yaa mice were stained with CD4, ICOS and CD200 antibodies for TFH cells and B220, IgM and Fas antibodies for GC B cells. The absolute numbers of TFH and GC B cells are shown in the right panel.
Figure 4:
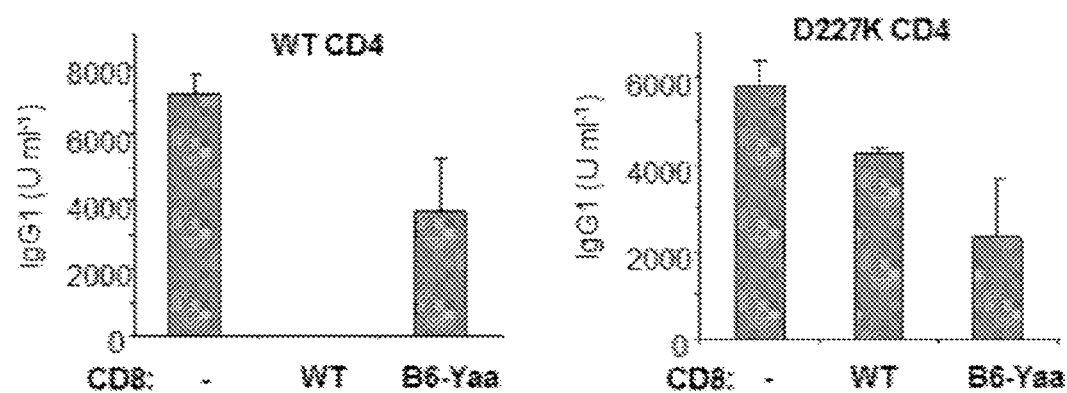
FIG. 4 shows the impaired suppression of Ab response by CD8$^+$ T cells from B6-Yaa mice. WT nave B cells were transferred along with CD25$^+$ depleted CD4 T cells from Qa-1 (WT) or Qa-1 (D227K) mice into Rag2$^{-/-}$ hosts. FACS sorted $CD44^+CD122^+$ CD8 T cells isolated from KLH/CFA immunized WT or B6-Yaa mice were transferred into Rag2$^{-/-}$ hosts. Immediately after cell transfer, Rag2$^{-/-}$ recipients were immunized i.p. with 100 µg NP19-KLH in CFA and reimmunized i.p. with 50 µg NP19-KLH in IFA 20 days later.
Figure 4:
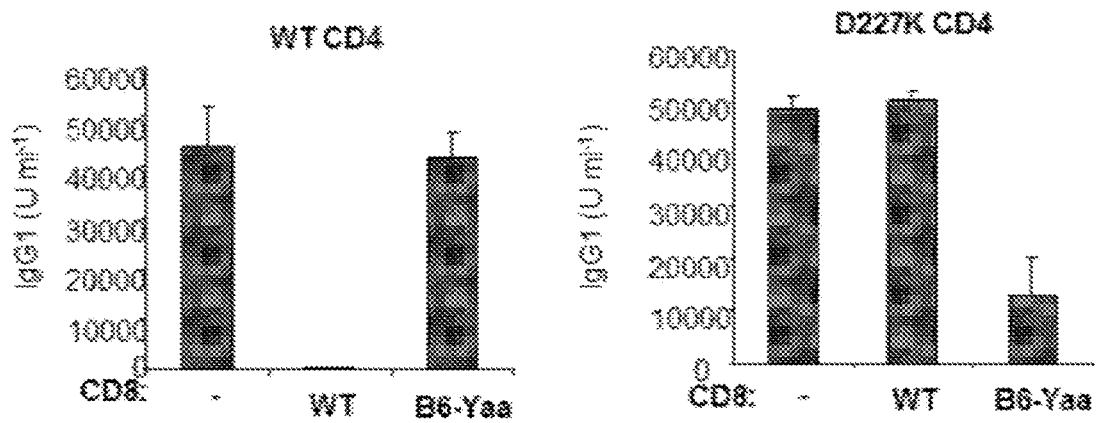

Defective CD8 Treg Function in B6-Yaa May Contribute to the Development of Lupus-Like Disease Expression of a point mutation that disrupts the interaction of Qa-1 ligands with the CD8/TCR complex (Lu et al., 2008) results in the development of a lupus-like autoimmune disorder in B6.Qa-1(D227K) mice associated with dysregulated expansion of $T_{FH}$ (Kim et al., 2010). Defective $CD8^+$ Treg activity may also contribute to disease pathogenesis in BXSB-Yaa mice based on findings that a cross between BXSB-Yaa mice and $B6.\beta_2 m^{-/-}$ mice shows accelerated onset and intensity of lupus-like disease (Bubier et al., 2007). The autoimmune disorder of BXSB-Yaa males, mainly attributed to a Y chromosome locus derived from the SB/Le strain, in fact represents an extra translocated copy of TLR7 onto the Y chromosome. This Y-linked extra copy of TLR7 exacerbates disease in a number of lupus-prone strains (Izui et al., 1988; Morel et al., 2000; Pisitkun et al., 2006) and promotes disease in non-autoimmune C57BL/6 background (B6-Yaa). Preliminary analysis of B6-Yaa mice showed that both 2 and 8 mo old mice harbored an approximate three-fold increase of $T_{FH}$ and GC B cells in spleen, reminiscent of the B6.Qa-1(D227K) phenotype (FIG. 3). We asked whether the autoimmune phenotype in B6-Yaa mice was associated with defective regulation by $CD8^+$ Treg. The numbers of $CD44^+CD122^+Ly49^+$ $CD8^+$ T cells in B6-Yaa mice were twice the number found in B6 WT mice 7 days after KLH/CFA immunization (data not shown). However, transfer of $CD44^+CD122^+$ $CD8^+$ Treg from B6-Yaa mice along with B6 (WT) CD4 cells and B cells into $Rag2^{-/-}$ hosts revealed that B6-Yaa CD8 Treg were unable to suppress target CD4 T cells. Since CD8 cells from WT mice transferred robust suppression in the same experiment (FIG. 4), this finding opens the possibility that $T_{FH}$ cell expansion associated with autoimmunity in B6-Yaa mice reflects defective CD8 Treg function.

Figure 7:
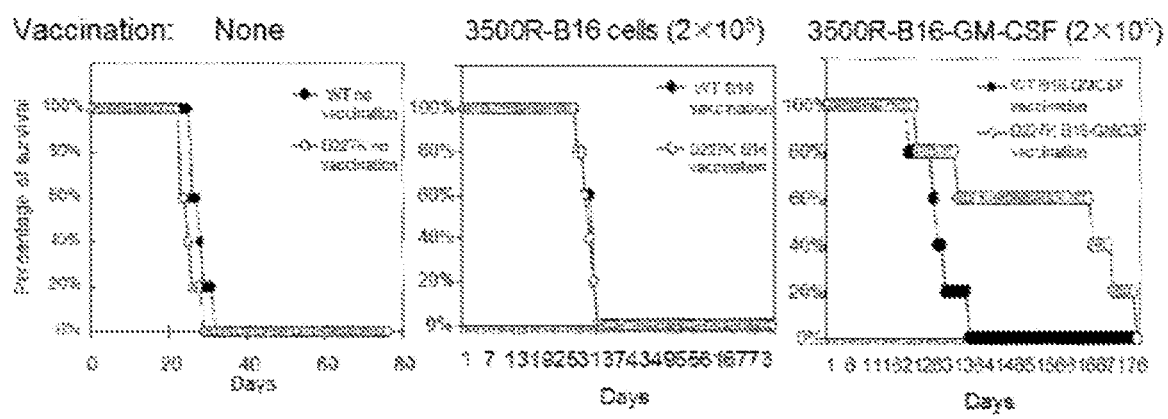
FIG. 7 shows that vaccination with $2\times10^5$ GM-CSF-irradiated (3500 rads) B16 cells confers increased survival after B16 tumor inoculation in Qa-1(D227K) knock in compared with WT B6 mice.
Figure 8A:
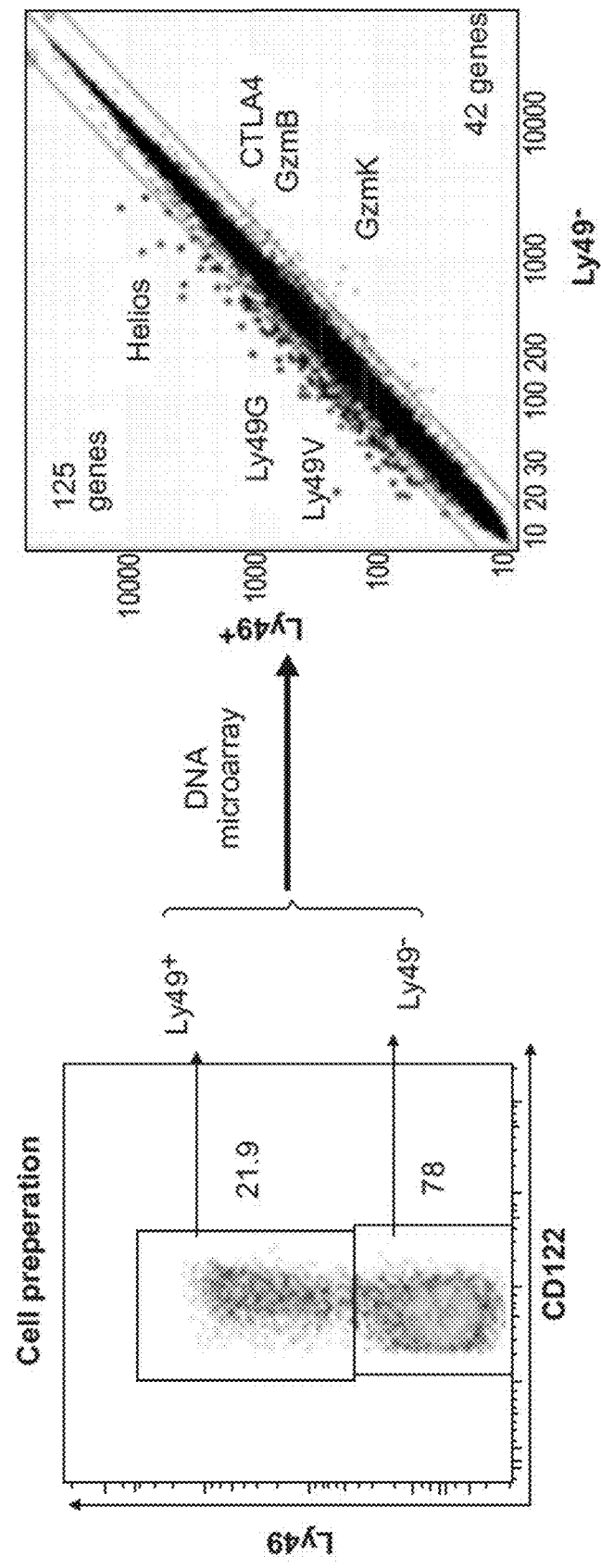
FIG. 8A shows a comparison of the gene expression profile between Ly49$^+$ and Ly49$^-CD44^+CD122^+CD8$ T cells by gene microarray analysis. B6 WT mice were immunized i.p. with KLH in CFA and Ly49$^+$ and Ly49$^-$ CD8 T cells were purified from spleen 7 days post immunization. Gene expression was analyzed using an Affymetrix microarray system and differential gene expression was assessed by Multiplot analysis program. 125 genes were upregulated and 42 genes were downregulated in Ly49+ cells compared to Ly49− cells.
Figure 8B:
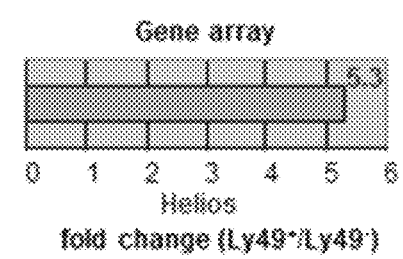
FIG. 8B shows the validation of Helios expression by RT-PCR: 5.3 fold increase of Helios expression was observed in Ly49+ CD8+ T cells in gene microarray analysis. Independent cDNA prepared from Ly49+ and Ly49− CD8 T cells were used to validate the increase of Helios expression in Ly49+ CD8 T cells by RT-PCR.
Figure 8B:
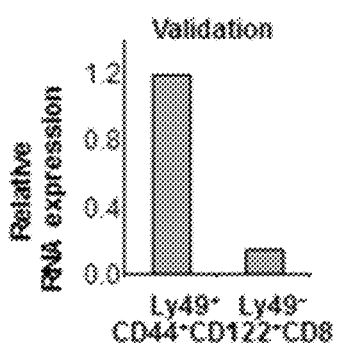
Figure 8C:
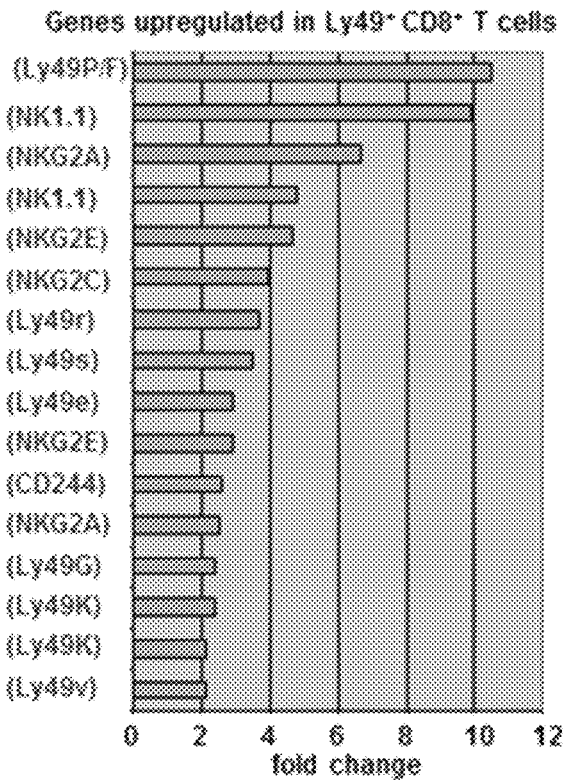
FIG. 8C shows that innate receptors are highly upregulated in Ly49+ CD8+ T cells: Gene expression profiling of Ly49+ CD8+ T cells in comparison to memory type Ly49− CD8 T cells revealed that receptors normally expressed in NK cells are prominently upregulated in Ly49+ T cells at mRNA level.
Figure 9A:
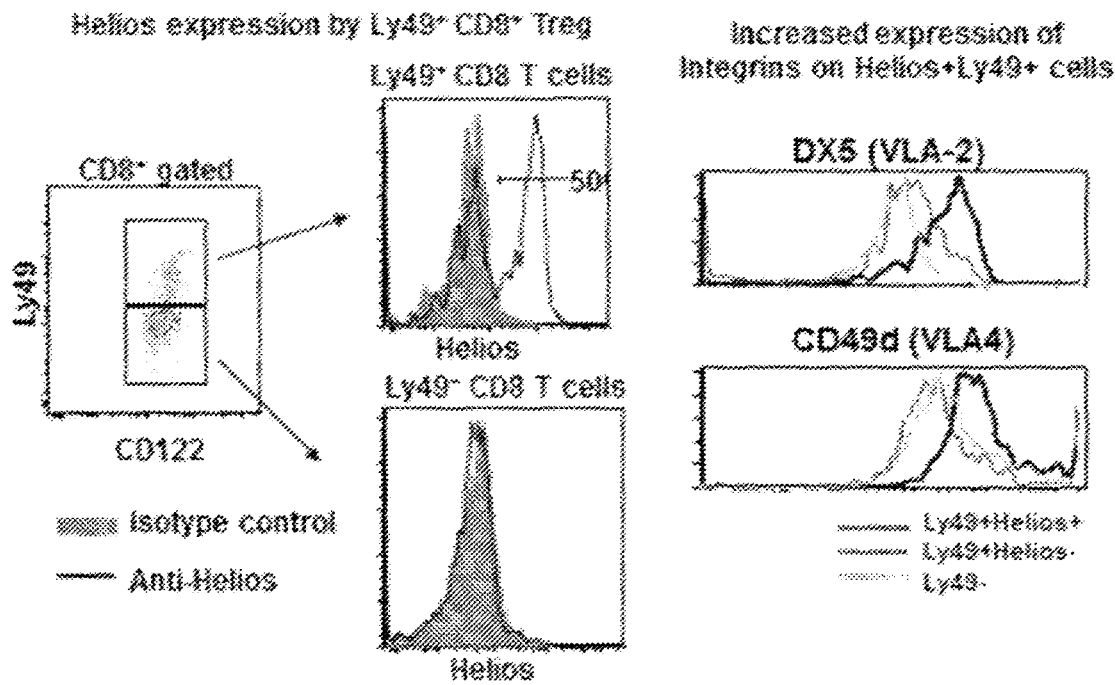
In FIG. 9A, FACS analysis of Ly49+ CD8 T cells revealed that Helios is expressed in 50% of Ly49+ CD8 T cells. Helios+ Ly49+ CD8 T cells display also higher level of integrin expression (VLA-2 and VLA-4) that may have functional significance in the cell contact dependent recognition of target cells.
Figure 9B:
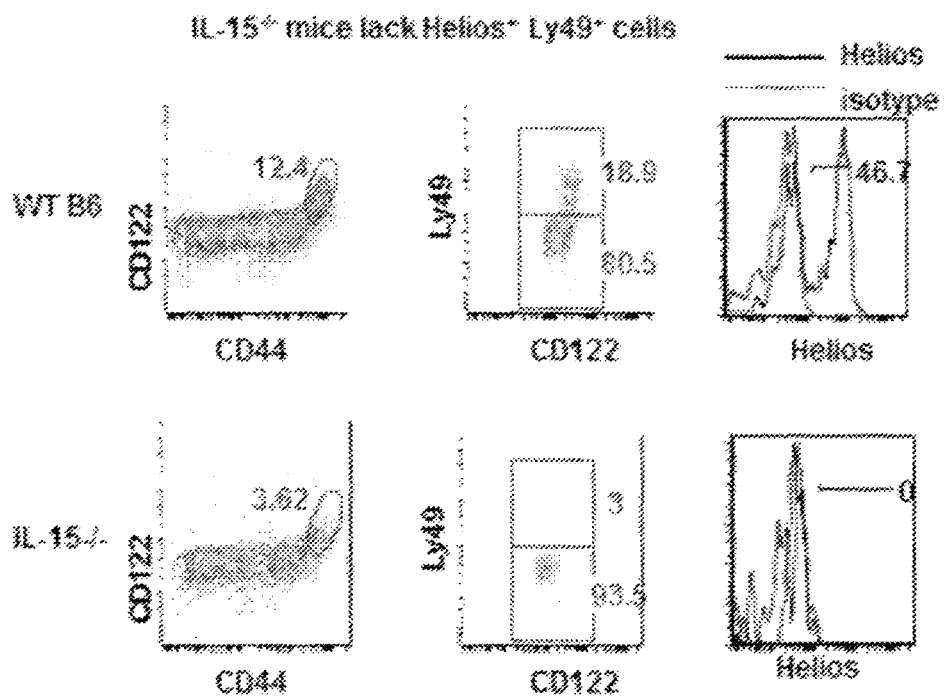
FIG. 9B shows the requirement of IL-15 for the development of Helios+Ly49+ CD8 T cells: IL-15 deficient mice show a dramatic reduction in Ly49+ CD8 T cells (18.9% of CD44+Cd122+ CD8 T cells in WT vs. 3% of CD44+CD12+ CD8 T cells in IL-15−/− mice). Ly49+ CD8+ T cells from Il-15−/− mice do not express Helios suggesting that the development of Helios Ly49+ CD8+ T cells is IL-15 dependent.
Figures 9C, 9D:
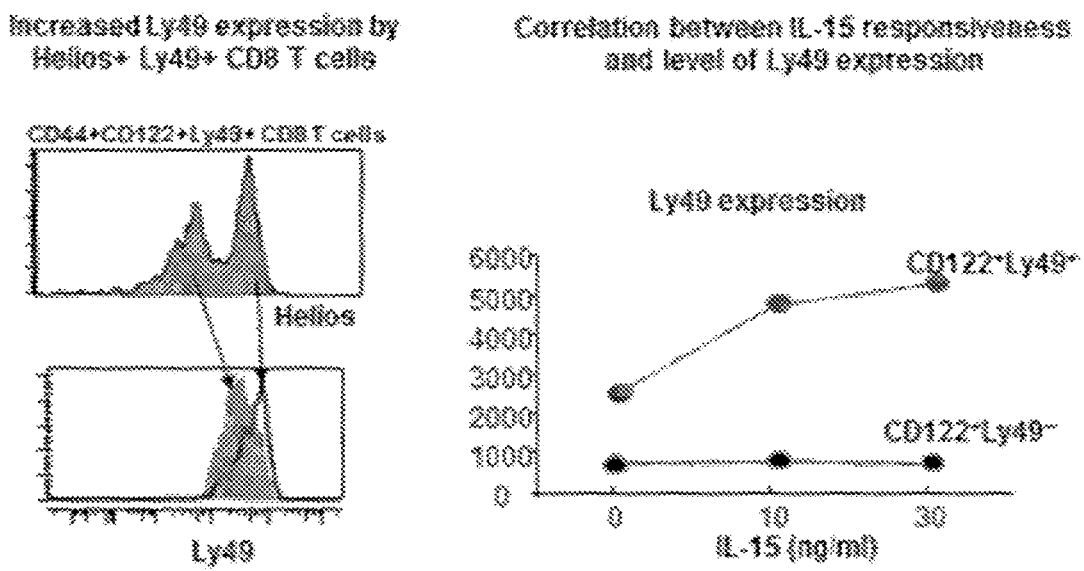
FIG. 9C shows the correlation between IL-15 responsiveness and level of Ly49 expression: Helios+ Ly49+ CD8 T cells may belong to the most IL-15 sensitive CD8 T cells. Helios+ Ly49+ CD8 T cells express higher level of CD122 and Ly49 compared to Helios− Ly49+ CD8 T cell counterpart. In vitro stimulation of Ly49+ CD8 T cells shows that Ly49+ expression is tightly associated with the strength of IL-15 stimulation. The extreme responsiveness of Helios+ Ly49+ CD8 T cells can be exploited in the in vitro expansion of CD8+ Treg using minute amount of IL-15 in the cell culture.
FIG. 9D shows that Helios deficient mice lack $Ly49^{h1}$ CD8 T cells: we have generated bone marrow (BM) chimera in which Rag2−/− mice were reconstituted with Helios WT or Helios KO BM cells. BM chimera generated with WT BM cells develop CD44+ CD122+ and CD44+CD122+Ly49+ CD8 T cells that are similar to WT B6 mice in their frequency. Helios KO BM chimera, however, show an increased CD44+CD122+ CD8 T cells and a dramatic reduction of Ly49+ CD8 T cells. FACS analysis for Helios expression confirms the Helios KO genotype.
Figure 9E:
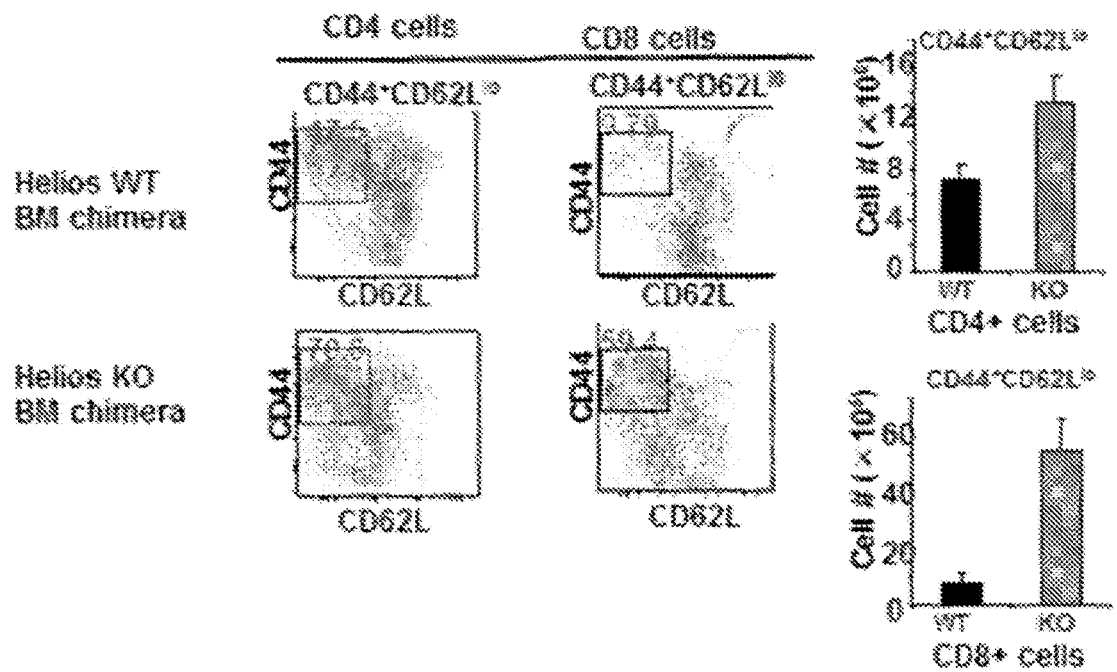
FIG. 9E shows the increase of activated CD4 and CD8 T cells in recipients of Helios KO BM cells: FACS analysis of spleen cells from Helios WT and KO BM revealed that Helios KO BM chimera have approximately 2 fold increase in activated CD4+ T cells)(CD4+CD44+ $CD62L^{lo}$) and 6 fold increase in activated CD8+ T cells) (CD8+CD44+$CD62L^{lo}$).
Figure 9F:
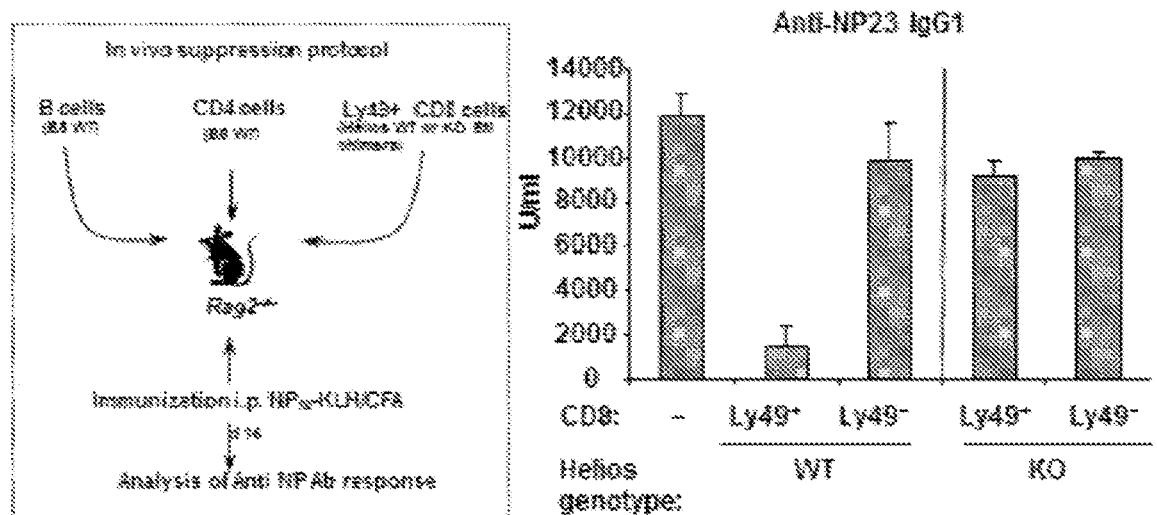
FIG. 9F shows the impaired suppressive activity of Helios deficient CD8+ T cells: Rag2−/− mice were transferred with B cells from WT B6 mice, CD25 depleted CD4+ T cells from WT B6 mice and Ly49+ CD8 T cells purified from Helios WT and KO BM chimera. Helios WT and KO BM chimera were immunized i.p. with KLH in CFA 7 days prior to CD8 preparation. Rag2−/− hosts were immunized i.p. with NP19-KLH/CFA immediately after cell transfer. While Rag2−/− hosts that received WT Ly49+ CD8 T cells show an efficient suppression of anti-NP Ab response, Helios KO Ly49+ CD8 T cell recipients show a similar level of anti-NP Ab response to Rag2−/− mice that did not receive CD8 T cells.

Vaccination with Suboptimal Levels of Irradiated B16-GM-CSF-Transduced Cells Confers Increased Survival after B16 Tumor Inoculation in Mice with Defective $CD8^+$ Treg Activity C57BL/6 Qa-1 (D227K) knock in mice and wild type C57BL/6 mice were vaccinated in one flank subcutaneously with $2\times10^5$ with GM-CSF-irradiated (3500 rads) B16 cells at time 0. One week after the vaccination, the mice were inoculated subcutaneously with $5\times10^6$ B16 melanoma cells in the opposite flank (Dranoff et al, Proc Natl Acad Sci USA. 1993 Apr. 15; 90(8):3539-43; Sampson et al, Proc Natl Acad Sci USA. 1996 Sep. 17; 93(19):10399-404). The C57BL/6 Qa-1 (D227K) knock in mice with defective $CD8^+$ Treg activity survived longer than the wild type C57BL/6 mice (FIG. 7).

A subpopulation of $CD8^+$ T cells programmed to regulate $CD4^+$ follicular helper T cell (TFH) activity through recognition of Qa-1 expressed at the surface of TFH cells dampens autoantibody responses (Kim et al., 2010; the entire content of which is incorporated by reference herein). Previous analysis of the surface phenotype of these $CD8^+$ regulatory (Treg) cells indicated that they expressed high levels of CD44 and CD122 and relatively lower levels of CXCR5 and ICOSL. Expression of CD122 on their surface is in accord with their dependence on IL-15 for both development and function (Kim et al., 2010). The regulatory activity is invested in the subpopulation of $CD44^+CD122^+$ $CD8^+$ cells that also express the Kir receptor. Expression of the class I MHC receptor by Ly49 by CD8 cells has been associated with enhanced responsiveness to IL-15 (Coles et al., 2000; Judge et al., 2002; Anfossi et al., 2004). These findings indicated that $CD44^+CD122^+Kir^+$ CD8 T cells, which represent 3-5% of CD8 T cells, account for virtually all of the Qa-1-restricted suppressive activity invested in this T cell subset.

Analysis of Qa-1 knock-in mice that express an amino acid exchange mutation (D→K) at position 227, which disrupts the interaction of Qa-1 ligands with the CD8/TCR complex, revealed defective $CD8^+$ Treg activity that was associated with expansion of TFH and GC B cells. These cellular abnormalities were associated with development of a lupus-like autoimmune disorder characterized by tissue-specific autoantibodies, lymphocyte infiltration of non-lymphoid organs and severe glomerulonephritis, a constellation of pathological changes similar to the syndrome displayed by BXSB-Yaa and C57BL/6-Yaa mice. The finding that BXSB-Yaa disease is exacerbated by the absence of β2m-associated class Ia/Ib proteins (Kim et al., 2010) also is consistent with the hypothesis that defective $CD8^+$ Treg activity might contribute to BXSB-Yaa disease. We find that within the first several months life B6-Yaa mice contain increased numbers of TFH and GC B cells, and $CD8^+$ Treg from these mice are unable to suppress WT CD4 T cells in adoptive hosts. Defects/abnormalities in the development of $CD8^+$ Treg cells may contribute to disease pathogenesis in this murine model of lupus.

Regulatory $CD8^+$ T cells are essential for maintenance of self-tolerance and inhibition of SLE-like autoimmune disease. The data presented herein establish the surface phenotype of CD8 Treg based on their dependence on the IL-15 cytokine for development and function. The results revealed that Qa-1-restricted suppressive activity of CD8 T cells is invested in a small subpopulation that expresses CD44, CD122 and Ly49 at their surface. In addition, we find that development of SLE-like disease in B6.Yaa autoimmune prone mice is associated with the defective regulatory activity of Qa-1-restricted CD8 Treg.

Qa-1, the mouse homolog of human leukocyte antigen E (HLA-E), forms a heterodimer with $\beta_2$-microglobulin that binds to and presents peptides derived from self or foreign proteins after deliberate immunization or infection (Lo et al., 1999; Lo et al., 2000; Sullivan et al., 2002). Although the mRNA encoding Qa-1 is detectable in many cell types (Transy et al., 1987), surface expression of the Qa-1-$\beta_2$-microglobulin heterodimer may be constrained by requirements for precise assembly and transport to the surface of activated T and B lymphocytes and dendritic cells (Sullivan et al., 2002; Soloski et al., 1995). Peptide-containing Qa-1 complexes engage two broad classes of receptors. Qa-1 heterodimers containing peptides derived from MHC class Ia leader sequences, called Qdm (for Qa-1 determinant modifier), bind to nonclonally distributed CD94-NKG2A receptors expressed by natural killer (NK) cells and a subpopulation of CD8 T cells. The functional consequence of Qa-1/Qdm-NKG2A interactions is generally inhibition of NK or CD8 cytolytic activity (Moser et al., 2002). A second class of Qa-1 ligand comprises Qa-1-$\beta_2$-microglobulin heterodimers that contain a growing list of peptides (Tompkins et al., 1998; Lo et al., 2000; Jiang et al., 2003; Davies et al., 2003). Interaction between this set of Qa-1 ligands and the TCR on CD8 T cells can promote CD8$^+$ Treg induction, population expansion and expression of effector cell activity.

Recent analysis of Qa-1 mutant mice has defined the essential contribution of CD8$^+$ Treg in the inhibition of autoimmune disease: the preferential target of CD8$^+$ Treg is the $T_{FH}$ subset, which expresses high steady-state levels of Qa-1 at their surface. Genetic disruption of the inhibitory interaction between CD8 Treg and target Qa-1$^+$ follicular helper T cells resulted in the development of a SLE-like autoimmune disease that was facilitated by stimulation with protein or viral antigens (Kim et al., 2010). Perforin and IL-15 have been shown to be required for the complete activity of CD8 Treg. An IL-15 dependent trans cytotoxic mechanism has been shown to be efficiently enhanced by IL-21, the canonical cytokine expressed by activated $T_{FH}$ cells (Zeng et al., 2005).

Our analysis revealed that CD8$^+$ Treg express inhibitory Ly49 receptors (Ly49A, Ly49G2, Ly49C/I, Ly49F), especially Ly49F (FIG. 2A), but not activating receptors. Earlier studies have shown that CD8 T cells expressing inhibitory Ly49 family members display a CD4-dependent increase with age, while STAT1-deficiency reduces the size of this Ly49$^+$ CD8 subpopulation (Coles et al., 2000; Anfossi et al., 2004). Although engagement of Ly49 can inhibit CD8 T cell activation (Coles et al., 2000), expression of inhibitory Ly49 molecules may also decrease activation induced cell death (AICD) and thus protect this memory population from premature elimination (Ugolini et al., 2001; Young et al., 2001; Roger et al., 2001; Chwae et al., 2002; Gati et al., 2003). These considerations suggest that inhibitory expression of Ly49 receptor on the surface of CD8$^+$ Treg may limit levels of initial activation but prolong their lifespan in the memory pool.

Interestingly, the ligand(s) that bind to the Ly49F receptor, the major Ly49 family member expressed by CD8$^+$ Treg, has not been identified. Lack of binding activity of Ly49F to conventional MHC class I molecules has led to speculation that this Ly49 family member may interact with non-classical MHC class I molecules (Kronenberg J I 2010). Human CD8 T cells also include a small subset of cells that expresses inhibitory KIR receptors, analogous to murine Ly49. Ly49 and KIR recognize mouse and human MHC class I, respectively. Ly49 proteins have a C-type lectin like domain in their extracellular domain, while the KIR family, as human NK inhibitory receptors, has an Immunoglobulin domain. Both proteins share structural homology with intracytoplasmic immunoreceptor tyrosine-based inhibitory motifs (ITIM), which deliver inhibitory signals upon binding to MHC class I by their respective KIR or Ly49 receptors (Vivier and Anfossi, 2004). KIR$^+$CD8$^+\alpha\beta^-$TCR$^+$ T cells express a memory phenotype but generally do not express CCR7 and cell surface CD28/CD27 (Mingari et al., 1996; Speiser et al., 1999; Anfossi et al., 2001). Interestingly, intracellular expression of perforin is confined to KIR$^+$ human CD8 T cells, representing 4-5% of the CD8$^+$ T cell pool from normal adults (Anfossi et al., 2004). Previous studies have shown that human CD8$^+$ T cell clones isolated from a small fraction of the KIR$^+$CD8$\alpha\beta^+$TCR$^+$ T cell pool (~4-5% of total CD8$^+$ T cells) recognize HLA-E (human homolog of Qa-1b), consistent with our findings that Ly49$^+$ CD8 T cells in mice exert Qa-1-dependent immune suppression (Pietra et al., 2001; Moretta et al., 2003; Mestas and Hughes, 2004).

Figure 5:
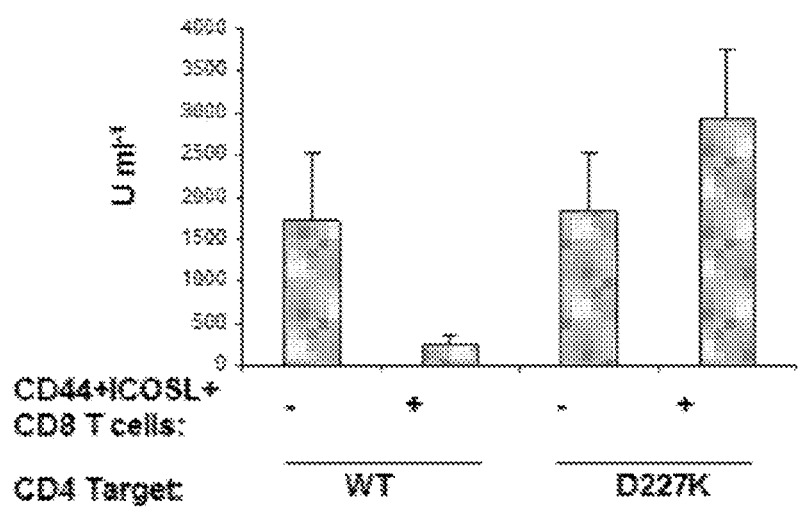
FIG. 5 shows the suppressive activity by $CD44^+ICOSL^+$ CD8 T cells. Ab response after transfer of B, CD4 and CD8 cells into Rag2$^{-/-}$ hosts. $2\times10^6$ WT nave B cells were transferred along with $0.5\times10^6$ CD25$^+$ depleted CD4 cells from B6.Qa-1(WT) or B6. Qa-1(D227K) mice into Rag2$^{-/-}$ hosts. $CD44^+ICOSL^+$ CD8$^+$ T cells were sorted by FACS from spleen cells of KLH/CFA immunized WT B6 mice. $0.15\times10^6$ sorted $CD44^+ICOSL^+$ CD8 cells were transferred into Rag2$^{-/-}$ hosts. Immediately after cell transfer, Rag2$^{-/-}$ recipients were immunized i.p. with 100 µg NP19-KLH in CFA. At day 10, mice were challenged i.p. with 50 µg NP19-KLH in IFA and high affinity NP specific Ab responses were measured by ELISA seven days after challenge.

We have noted that CD44$^+$CD122$^+$ cells express CXCR5 and ICOSL, according to bead-dependent enrichment (Kim et al., 2010) and FACS-dependent cell sorting (FIG. 5). This surface phenotype is of interest because of its potential contribution to suppressive activity of CD8$^+$ Treg. CXCR5 expression may allow navigation of CD8$^+$ Treg to the B/CD4 T cell follicles, while expression of ICOSL by activated emigrant CD8 Treg may enhance its interaction with ICOS$^+$ $T_{FH}$ cells within the follicular microenvironment. However, detection of these two surface proteins by available antibodies is relatively inefficient, while antibodies specific for CD44, CD122, and Ly49 are preferable for efficient isolation of CD8 Treg from heterogeneous cell populations. Sorting of CD8$^+$ cells based on expression of the triad of CD44, CD122 and Ly49 will facilitate further analysis of the molecular mechanism of suppression and definition of the genetic signature of this regulatory lineage in B6 mice.

The Yaa genetic modifier, which increases severity of SLE in male mice, was first identified from a cross between C57BL/6 female and SB/Le male that produced the BXSB hybrid line. In addition to BXSB strain, the Yaa Y chromosome exacerbates disease in a number of lupus-prone strains (Kikuchi et al., 2005; Subramanian et al., 2006). Introgression of Yaa onto the non-autoimmune B6 background (B6-Yaa) revealed that Yaa could produce SLE-like disease at 8-12 m of age characterized by lupus nephritis. Although end organ autoimmune disease does not develop in B6-Yaa mice until 8-12 m, we find that expansion of $T_{FH}$ and GC B cells is apparent by 2 m after birth (FIG. 5). Accumulation of $T_{FH}$ and GC B cells at this early stage was associated with defective regulatory activity of CD8 T cells. Chronic activation of CD8$^+$ memory cells by activated TLR7$^{hi}$ DC may preferentially support development of cytokine-secreting CD8$^+$ memory cells rather than CD8$^+$ regulatory cells.

The IL-15 dependence of Qa-1-restricted CD8 Treg cells is reflected in co-expression of CD122 and Kir and that CD44$^+$CD122$^+$Ly49$^+$ CD8 cells mediate Qa-1-dependent suppressive activity. Interruption of the interaction between CD8 Treg and target CD4 T cells results in autoantibody generation and SLE-like disease. These findings indicate that enhancement of CD8 Treg activity represents a new approach to treatment of autoimmune disease.

Expression of the Transcription Factor Helios Dictates the Phenotype and Suppressive Activity of Ly49+ CD8 Treg DNA microarray with cDNA prepared from Ly49+ and Ly49− CD8+ T cells identified the transcription factor Helios as a potential master transcription factor for genes that are important for the CD8 Treg development and function. Helios is one of the Ikaros family members of zinc finger regulator. Helios is highly expressed at early stage of T cell development and also expressed in a subset (~70%) of FoxP3+CD4+ Treg cells; however, Helios expression is not dependent on FoxP3 expression. Mature B cells, dendritic cells and myeloid cells do not express Helios. Helios expression and function in CD8 T cell pool has not been reported. Our analysis shows that Helios is exclusively expressed by Ly49+ CD8 Treg cells within CD8 T cell pool and expression of this transcription factor in Ly49+ T cell is associated with their suppressive function (FIG. 8).

Phenotypic Characterization of Helios Expressing Ly49+ CD8 T Cells

Additional characterization of Helios+Ly49+ murine CD8+ Treg is helpful for the future identification of KIR+ CD8+ Treg cells in human. As demonstrated in FIG. 9, Helios expressing Ly49+ CD8 cells express higher level of VLA-2 and VLA-4, integrins that are involved in the cell-cell interaction. In addition, development of Helios+Ly49+ CD8 T cells is IL-15 dependent, since IL-15 KO mice are devoid of Helios+Ly49+ CD8 cells. Analysis of a critical transcription factor, Helios, for CD8 Treg activity in mouse adds one more important factor for the identification of CD8+ Treg cells in human and for the understanding their genetic nature.

CD8 Treg Mediated Immunotherapy in Autoimmune Disease: CIA Model

Pathogenic CD4+ T cells associated with organ-specific autoimmune diseases can be effectively suppressed via recognition of Qa-1 expressed by these target CD4+ cells by CD8+ Treg. These autoimmune disease models include Type I diabetes (T1D), experimental autoimmune encephalomyelitis (EAE) and collagen-induced arthritis (CIA) in which conventional TH1- and/or TH17-type CD4 cells are known to play a pathogenic role. We have tested the efficacy of CD8 Treg in the prevention and treatment of autoimmune disease using collagen induced arthritis model. Development of disease can be delayed by infusion of Qa-1-restricted CD8+ Treg, but not by memory-phenotype CD8+ T cells.

Figure 10A:
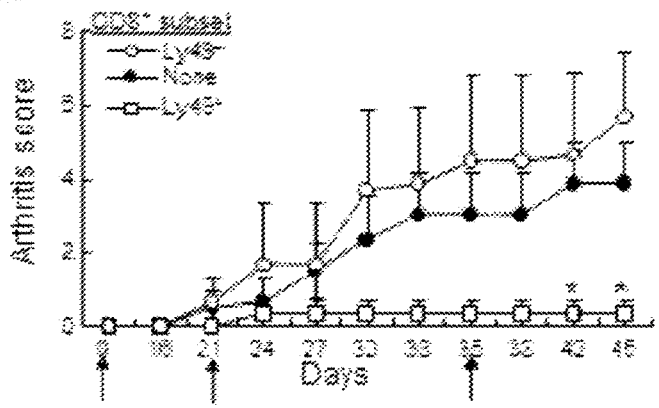
FIG. 10A shows the prevention of CIA by infusion of CD8+ Treg: WT B and CD25 depleted CD4 cells were sorted from spleen cells of WT B6 mice. Ly49+ and Ly49− CD8 T cells are sorted from spleen and lymph nodes. Collagen type II cells were transferred into Rag2−/− Prf1−/− mice followed by arthritis induction at d0 and boosted at d21. CD8 Treg were infused at d21 and d35 additionally. CIA development was monitored. Sorted CD44+CD122+Ly49+ or Ly49− CD8 cells were cultured in the presence of 2 ng/ml IL-15/IL-15Rα complex for 1 week. Rag2−/− Prf1−/− mice were transferred with B, CD4 and in vitro expanded CD8 T cells (d0, 21 and 35) and CIA development monitored in FIG. 10B.
Figure 10B:
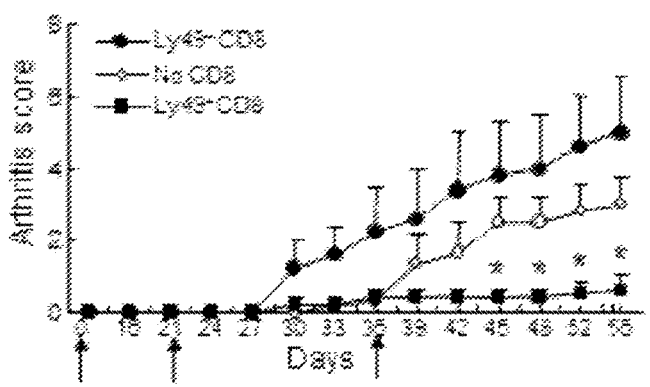
FIG. 10 shows CD8 Treg-mediated immunotherapy in autoimmune disease: CIA model.
FIG. 10C shows a therapeutic application of CD8 Treg: $1.5 \times 10^5$ in vitro expanded Ly49+ CD8 T cells were transferred into B6 mice that developed arthritis in an average score of 3.5 at d 0 and d18. 0.75 mg/kg methotrexate (MTX) was given from d5 to d17 every two days.
Figure 10C:
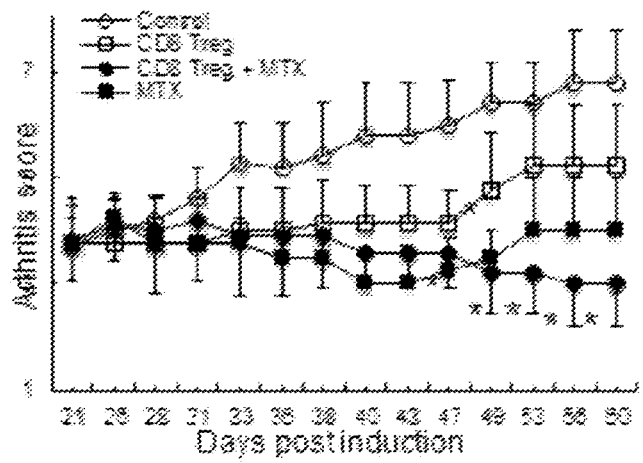

Stimulation of CD8+ Treg by IL-15 in vitro results in robust expansion of these cells and maintenance of surface phenotype and functional activity. In FIG. 10, in vitro expanded CD8 Treg efficiently prevent the development of CIA.

CD8 Treg Mediated Immunotherapy in Cancer

Blockade of CD8+ Treg activity led to enhanced tumor immunity in B16 melanoma model: vaccination of mice with GM-CSF-producing B16 melanoma delayed the progression of tumor growth in Qa-1 D227K mice compared to rapid tumor growth in WT mice. Inhibition of tumor growth in Qa-1 D227K mice correlated with increased numbers of CD8+ effector T cell infiltration into tumors. Therefore, blockade of CD8+ Treg-dependent suppression will result in enhanced expansion and activity of effector T cells in tumor setting. To deplete CD8+ Treg, the expression of Ly49F subtype by more than 90% of Ly49+ CD8 Treg can be exploited. In fact, preliminary data has shown that depletion of Ly49F+ cells by anti-Ly49F antibody enhances anti-tumor immunity in B16 melanoma model. This finding suggests that administration of anti-KIR(X) antibody (antibody targeting the dominant KIR subtype in CD8 T cells in human) is a feasible intervention to enhance immune responses against cancer in human.

This invention is not limited in its application to the details of construction and the arrangement of components set forth in the above description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

REFERENCES

Anderton, S. M., Radu, C. G., Lowrey, P. A., Ward, E. S., and Wraith, D. C. (2001). Negative selection during the peripheral immune response to antigen. J Exp. Med. 193, 1-11.

Anfossi, N., Pascal, V., Vivier, E., and Ugolini, S. (2001). Biology of T memory type 1 cells. Immunol. Rev. 181, 269-278.

Anfossi, N., Robbins, S. H., Ugolini, S., Georgel, P., Hoebe, K., Bouneaud, C., Ronet, C., Kaser, A., DiCioccio, C. B., Tomasello, E., Blumberg, R. S., Beutler, B., Reiner, S. L., Alexopoulou, L., Lantz, O., Raulet, D. H., Brossay, L., and Vivier, E. (2004). Expansion and function of CD8+ T cells expressing Ly49 inhibitory receptors specific for MHC class I molecules. J. Immunol. 173, 3773-3782.

Bouneaud, C., Kourilsky, P., and Bousso, P. (2000). Impact of negative selection on the T cell repertoire reactive to a self-peptide: a large fraction of T cell clones escapes clonal deletion. Immunity 13, 829-840.

Bubier, J. A., Bennett, S. M., Sproule, T. J., Lyons, B. L., Olland, S., Young, D. A., and Roopenian, D. C. (2007). Treatment of BXSB-Yaa mice with IL-21R-Fc fusion protein minimally attenuates systemic lupus erythematosus. Ann. N. Y. Acad. Sci. 1110, 590-601.

Chwae, Y. J., Chang, M. J., Park, S. M., Yoon, H., Park, H. J., Kim, S. J., and Kim, J. (2002). Molecular mechanism of the activation-induced cell death inhibition mediated by a p70 inhibitory killer cell Ig-like receptor in Jurkat T cells. J. Immunol. 169, 3726-3735.

Coles, M. C., McMahon, C. W., Takizawa, H., and Raulet, D. H. (2000). Memory CD8 T lymphocytes express inhibitory MHC-specific Ly49 receptors. Eur. J. Immunol. 30, 236-244.

Davies, A., Kalb, S., Liang, B., Aldrich, C. J., Lemonnier, F. A., Jiang, H., Cotter, R., and Soloski, M. J. (2003). A peptide from heat shock protein 60 is the dominant peptide bound to Qa-1 in the absence of the MHC class Ia leader sequence peptide Qdm. J. Immunol. 170, 5027-5033.

Gati, A., Guerra, N., Gaudin, C., Da Rocha, S., Escudier, B., Lecluse, Y., Bettaieb, A., Chouaib, S., and Caignard, A. (2003). CD158 receptor controls cytotoxic T-lymphocyte susceptibility to tumor-mediated activation-induced cell death by interfering with Fas signaling. Cancer Res. 63, 7475-7482.

Goldrath, A. W. and Bevan, M. J. (1999). Selecting and maintaining a diverse T-cell repertoire. Nature 402, 255-262.

Izui, S., Higaki, M., Morrow, D., and Merino, R. (1988). The Y chromosome from autoimmune BXSB/MpJ mice induces a lupus-like syndrome in (NZW×C57BL/6)F1 male mice, but not in C57BL/6 male mice. Eur. J. Immunol. 18, 911-915.

Jiang, H., Curran, S., Ruiz-Vazquez, E., Liang, B., Winchester, R., and Chess, L. (2003). Regulatory CD8+ T cells fine-tune the myelin basic protein-reactive T cell receptor V beta repertoire during experimental autoimmune encephalomyelitis. Proc. Natl. Acad. Sci. U.S.A 100, 8378-8383.

Judge, A. D., Zhang, X., Fujii, H., Surh, C. D., and Sprent, J. (2002). Interleukin 15 controls both proliferation and survival of a subset of memory-phenotype CD8(+) T cells. J. Exp. Med. 196, 935-946.

Kearney, E. R., Pape, K. A., Loh, D. Y., and Jenkins, M. K. (1994). Visualization of peptide-specific T cell immunity and peripheral tolerance induction in vivo. Immunity 1(4), 327-339.

Kikuchi, S., Fossati-Jimack, L., Moll, T., Amano, H., Amano, E., Ida, A., Ibnou-Zekri, N., Laporte, C., Santiago-Raber, M. L., Rozzo, S. J., Kotzin, B. L., and Izui, S. (2005). Differential role of three major New Zealand Black-derived loci linked with Yaa-induced murine lupus nephritis. J. Immunol. 174, 1111-1117.

Kim, H. J., Verbinnen, B., Tang, X., Lu, L., and Cantor, H. (2010). Inhibition of follicular T helper cells by CD8+ Treg is essential for self tolerance. Nature 467, 328-332.

Littman, D. R. and Rudensky, A. Y. (2010). Th17 and regulatory T cells in mediating and restraining inflammation. Cell 140, 845-858.

Lo, W. F., Ong, H., Metcalf, E. S., and Soloski, M. J. (1999). T cell responses to gram-negative intracellular bacterial pathogens: a role for CD8+ T cells in immunity to *Salmonella* infection and the involvement of MHC class Ib molecules. J. Immunol. 162, 5398-5406.

Lo, W. F., Woods, A. S., DeCloux, A., Cotter, R. J., Metcalf, E. S., and Soloski, M. J. (2000). Molecular mimicry mediated by MHC class Ib molecules after infection with gram-negative pathogens. Nat. Med. 6, 215-218.

Lu, L., Kim, H. J., Werneck, M. B., and Cantor, H. (2008). Regulation of CD8+ regulatory T cells: Interruption of the NKG2A-Qa-1 interaction allows robust suppressive activity and resolution of autoimmune disease. Proc. Natl. Acad. Sci. U.S.A 105, 19420-19425.

Martin, D. A., Zheng, L., Siegel, R. M., Huang, B., Fisher, G. H., Wang, J., Jackson, C. E., Puck, J. M., Dale, J., Straus, S. E., Peter, M. E., Krammer, P. H., Fesik, S., and Lenardo, M. J. (1999). Defective CD95/APO-1/Fas signal complex formation in the human autoimmune lymphoproliferative syndrome, type Ia. Proc. Natl. Acad. Sci. U.S.A. 96, 4552-4557.

Mestas, J. and Hughes, C. C. (2004). Of mice and not men: differences between mouse and human immunology. J. Immunol. 172, 2731-2738.

Mingari, M. C., Schiavetti, F., Ponte, M., Vitale, C., Maggi, E., Romagnani, S., Demarest, J., Pantaleo, G., Fauci, A. S., and Moretta, L. (1996). Human CD8+ T lymphocyte subsets that express HLA class I-specific inhibitory receptors represent oligoclonally or monoclonally expanded cell populations. Proc. Natl. Acad. Sci. U.S.A 93, 12433-12438.

Morel, L., Croker, B. P., Blenman, K. R., Mohan, C., Huang, G., Gilkeson, G., and Wakeland, E. K. (2000). Genetic reconstitution of systemic lupus erythematosus immunopathology with polycongenic murine strains. Proc. Natl. Acad. Sci. U.S.A 97, 6670-6675.

Moretta, L., Romagnani, C., Pietra, G., Moretta, A., and Mingari, M. C. (2003). NK-CTLs, a novel HLA-E-restricted T-cell subset. Trends Immunol. 24, 136-143.

Moser, J. M., Gibbs, J., Jensen, P. E., and Lukacher, A. E. (2002). CD94-NKG2A receptors regulate antiviral CD8 (+) T cell responses. Nat. Immunol. 3, 189-195.

Panoutsakopoulou, V., Sanchirico, M. E., Huster, K. M., Jansson, M., Granucci, F., Shim, D. J., Wucherpfennig, K. W., and Cantor, H. (2001). Analysis of the Relationship between Viral Infection and Autoimmune Disease. Immunity 15, 137-147.

Pietra, G., Romagnani, C., Falco, M., Vitale, M., Castriconi, R., Pende, D., Millo, E., Anfossi, S., Biassoni, R., Moretta, L., and Mingari, M. C. (2001). The analysis of the natural killer-like activity of human cytolytic T lymphocytes revealed HLA-E as a novel target for TCR alpha/beta-mediated recognition. Eur. J. Immunol. 31, 3687-3693.

Pisitkun, P., Deane, J. A., Difilippantonio, M. J., Tarasenko, T., Satterthwaite, A. B., and Bolland, S. (2006). Autoreactive B cell responses to RNA-related antigens due to TLR7 gene duplication. Science 312, 1669-1672.

Roger, J., Chalifour, A., Lemieux, S., and Duplay, P. (2001). Cutting edge: Ly49A inhibits TCR/CD3-induced apoptosis and IL-2 secretion. J. Immunol. 167, 6-10.

Slifka, M. K., Blattman, J. N., Sourdive, D. J., Liu, F., Huffman, D. L., Wolfe, T., Hughes, A., Oldstone, M. B., Ahmed, R., and von Herrath, M. G. (2003). Preferential escape of subdominant CD8+ T cells during negative selection results in an altered antiviral T cell hierarchy. J. Immunol. 170, 1231-1239.

Soloski, M. J., DeClou, A., Aldrich, C. J., and Forman, J. (1995). Structural and functional characteristics of the class 1B molecule, Qa-1. Immunol. Rev. 147, 67-89.

Speiser, D. E., Pittet, M. J., Valmori, D., Dunbar, R., Rimoldi, D., Lienard, D., MacDonald, H. R., Cerottini, J. C., Cerundolo, V., and Romero, P. (1999). In vivo expression of natural killer cell inhibitory receptors by human melanoma-specific cytolytic T lymphocytes. J. Exp. Med. 190, 775-782.

Subramanian, S., Tus, K., Li, Q. Z., Wang, A., Tian, X. H., Zhou, J., Liang, C., Bartov, G., McDaniel, L. D., Zhou, X. J., Schultz, R. A., and Wakeland, E. K. (2006). A Tlr7 translocation accelerates systemic autoimmunity in murine lupus. Proc. Natl. Acad. Sci. U.S.A 103, 9970-9975.

Sullivan, B. A., Kraj, P., Weber, D. A., Ignatowicz, L., and Jensen, P. E. (2002). Positive selection of a Qa-1-restricted T cell receptor with specificity for insulin. Immunity 17, 95-105.

Tompkins, S. M., Kraft, J. R., Dao, C. T., Soloski, M. J., and Jensen, P. E. (1998). Transporters associated with antigen processing (TAP)-independent presentation of soluble insulin to alpha/beta T cells by the class Ib gene product, Qa-1(b). J. Exp. Med. 188, 961-971.

Transy, C., Nash, S. R., David-Watine, B., Cochet, M., Hunt, S. W., Hood, L. E., and Kourilsky, P. (1987). A low polymorphic mouse H-2 class I gene from the Tla complex is expressed in a broad variety of cell types. J. Exp. Med. 166, 341-361.

Ugolini, S., Arpin, C., Anfossi, N., Walzer, T., Cambiaggi, A., Forster, R., Lipp, M., Toes, R. E., Melief, C. J., Marvel, J., and Vivier, E. (2001). Involvement of inhibitory NKRs in the survival of a subset of memory-phenotype CD8+ T cells. Nat. Immunol. 2, 430-435.

Vivier, E. and Anfossi, N. (2004). Inhibitory NK-cell receptors on T cells: witness of the past, actors of the future. Nat. Rev. Immunol 4, 190-198.

Young, N. T., Uhrberg, M., Phillips, J. H., Lanier, L. L., and Parham, P. (2001). Differential expression of leukocyte receptor complex-encoded Ig-like receptors correlates with the transition from effector to memory CTL. J. Immunol. 166, 3933-3941.

Zeng, R., Spolski, R., Finkelstein, S. E., Oh, S., Kovanen, P. E., Hinrichs, C. S., Pise-Masison, C. A., Radonovich, M. F., Brady, J. N., Restifo, N. P., Berzofsky, J. A., and Leonard, W. J. (2005). Synergy of IL-21 and IL-15 in regulating CD8+ T cell expansion and function. J. Exp. Med. 201, 139-148.

We claim:

1. A method for treating an autoimmune disease in a subject comprising:
   a. isolating and enriching T cells from the subject in need of such treatment to provide a T cell population, wherein at least 10% of the T cell population are CD44+CD122+Kir+CD8αβ+ Treg cells; and
   b. administering the T cell population containing the at least 10% CD44+CD122+Kir+CD8αβ+ Treg cells to the subject in an amount effective to ameliorate a symptom of the autoimmune disease.

2. The method of claim 1, wherein at least 20% of the isolated and enriched T cells are CD44+CD122+Kir+CD8αβ+ Treg cells.

3. The method of claim 1, wherein at least 50% of the isolated and enriched T cells are CD44+CD122+Kir+CD8αβ+ Treg cells.

4. The method of claim 1, wherein at least 90% of the isolated and enriched T cells are CD44+CD122+Kir+CD8αβ+ Treg cells.

5. The method of claim 1, wherein the CD44+CD122+Kir+CD8αβ+ Treg cells are Helios+.

6. The method of claim 1, wherein the CD44+CD122+Kir+CD8αβ+ Treg cells are administered by intravenous injection.

7. The method of claim 1, wherein the isolated and enriched cells are enriched by depleting a population of non-CD44+CD122+Kir+CD8αβ+ Treg cells.

8. The method of claim 1, wherein the isolated and enriched cells are enriched by sorting for CD44+CD122+Kir+CD8αβ+ Treg cells.

* * * * *

SEQUENCE LISTING

<160> NUMBER OF SEQ ID NOS: 1

<210> SEQ ID NO 1
<211> LENGTH: 162
<212> TYPE: PRT
<213> ORGANISM: Homo sapiens

<400> SEQUENCE: 1

```
Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
            35                  40                  45

Asn Trp Val Asn Val Ile Ser Asp Leu Lys Lys Ile Glu Asp Leu Ile
        50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
                100                 105                 110

Asn Leu Ile Ile Leu Ala Asn Asn Ser Leu Ser Ser Asn Gly Asn Val
            115                 120                 125

Thr Glu Ser Gly Cys Lys Glu Cys Glu Glu Leu Glu Glu Lys Asn Ile
        130                 135                 140

Lys Glu Phe Leu Gln Ser Phe Val His Ile Val Gln Met Phe Ile Asn
145                 150                 155                 160

Thr Ser
```